US012788263B2

(12) United States Patent
Johnson et al.

(10) Patent No.: US 12,788,263 B2
(45) Date of Patent: Nov. 10, 2026

(54) PREDICTING FRACTIONAL FLOW RESERVE FROM ELECTROCARDIOGRAMS AND PATIENT RECORDS

(71) Applicant: Tempus AI, Inc., Chicago, IL (US)

(72) Inventors: Kipp Johnson, Chicago, IL (US); Tanner Carbonati, Chicago, IL (US)

(73) Assignee: Tempus AI, Inc., Chicago, IL (US)

(*) Notice: Subject to any disclaimer, the term of this patent is extended or adjusted under 35 U.S.C. 154(b) by 765 days.

(21) Appl. No.: 17/537,481

(22) Filed: Nov. 29, 2021

(65) Prior Publication Data

US 2022/0183571 A1 Jun. 16, 2022

Related U.S. Application Data

(60) Provisional application No. 63/124,508, filed on Dec. 11, 2020.

(51) Int. Cl.

| | |
|---|---|
| ***A61B 5/026*** | (2006.01) |
| ***A61B 5/00*** | (2006.01) |
| ***A61B 5/318*** | (2021.01) |
| ***G16H 50/20*** | (2018.01) |

(52) U.S. Cl.

CPC ............ *A61B 5/026* (2013.01); *A61B 5/0006* (2013.01); *A61B 5/318* (2021.01); *A61B 5/7267* (2013.01); *A61B 5/7275* (2013.01); *A61B 5/742* (2013.01); *A61B 5/7475* (2013.01); *G16H 50/20* (2018.01)

(58) Field of Classification Search

CPC ....... A61B 5/026; A61B 5/318; A61B 5/0006; A61B 5/7267; A61B 5/7275; G16H 50/20

See application file for complete search history.

(56) References Cited

U.S. PATENT DOCUMENTS

| | | | | |
|---|---|---|---|---|
| 2016/0300350 | A1 | 10/2016 | Choi | |
| 2016/0364526 | A1 | 12/2016 | Reicher | |
| 2017/0119272 | A1* | 5/2017 | Gupta ................ | A61B 5/14551 |
| 2018/0336319 | A1 | 11/2018 | Itu | |
| 2019/0318476 | A1 | 10/2019 | Isgum | |
| 2019/0336096 | A1 | 11/2019 | Itu | |
| 2020/0098448 | A1 | 3/2020 | Shah | |
| 2021/0064936 | A1* | 3/2021 | Itu ....................... | G06F 18/2178 |
| 2021/0076960 | A1 | 3/2021 | Fornwalt | |

(Continued)

FOREIGN PATENT DOCUMENTS

| | | |
|---|---|---|
| WO | 2021055870 A1 | 3/2021 |
| WO | 2021097393 A1 | 5/2021 |
| WO | 2021097460 A1 | 5/2021 |

OTHER PUBLICATIONS

International Searching Authority. International Search Report and Written Opinion for application PCT/US2021/062664. Mailed on Mar. 11, 2022. 7 pages.

(Continued)

*Primary Examiner* — Puya Agahi

(74) *Attorney, Agent, or Firm* — Quarles & Brady LLP

(57) ABSTRACT

Computer-implemented systems and methods are provided for supplying electrocardiograms and identified patient information to an artificial intelligence engine comprising a neural network configured with a fractional flow reserve prediction model and that predicts a calculated fractional flow reserve for the patient, from which a predicted occurrence of one or more cardiac events is determined.

30 Claims, 15 Drawing Sheets

(56) References Cited

U.S. PATENT DOCUMENTS

| | | | |
|---|---|---|---|
| 2021/0090694 | A1 | 3/2021 | Colley |
| 2021/0145404 | A1 | 5/2021 | Fornwalt |
| 2021/0150693 | A1 | 5/2021 | Fornwalt |
| 2021/0151191 | A1 | 5/2021 | Fornwalt |

OTHER PUBLICATIONS

Provisional U.S. Appl. No. 63/139,923, entitled ECG-Based Cardiovascular Disease Detection System and Methods. Filed May 28, 2021.

Alizadehsani, Roohallah, et al. "Diagnosis of coronary arteries stenosis using data mining." Journal of Medical Signals & Sensors 2.3 (2012): 153-159.

Alizadehsani, Roohallah, et al. "Non-invasive detection of coronary artery disease in high-risk patients based on the stenosis prediction of separate coronary arteries." Computer methods and programs in biomedicine 162 (2018): 119-127.

Kwon, Joon-Myoung, et al. "Deep learning-based algorithm for detecting aortic stenosis using electrocardiography." Journal of the American Heart Association 9.7 (2020): e014717.

Phadke, Gautam, Mohammad Reza Rajati, and Leena Phadke. "Prediction of coronary artery disease using electrocardiogramachine learning approach." 2020 International Conference on Machine Learning and Cybernetics (ICMLC). IEEE, 2020.

Extended European Search Report in European Application No. 21904418.7; received on Oct. 1, 2024.

* cited by examiner

900

920

PREDICTING FRACTIONAL FLOW RESERVE FROM ELECTROCARDIOGRAMS AND PATIENT RECORDS

CROSS-REFERENCE TO RELATED APPLICATIONS

This application claims the benefit of priority to U.S. provisional patent application No. 63/124,508, filed Dec. 11, 2020.

FIELD OF THE INVENTION

The present disclosure relates to computer-implemented methods and systems for predicting fractional flow reserve based on computational analysis of a patient's electrocardiograms and medical records.

BACKGROUND

Extracting meaningful medical features from an ever-expanding quantity of health information tabulated for a similarly expanding cohort of patients having a multitude of sparsely populated features is a difficult endeavor. Identifying which medical features, from the tens of thousands of features available in health information, are most probative to training and utilizing a prediction engine only compounds the difficulty. Features which may be relevant to predictions may only be available in a small subset of patients and features which are not relevant may be available in many patients. What is needed is a system that may ingest these impossibly comprehensive scopes of available data across entire populations of patients to identify features which apply to the largest number of patients and establish a model for prediction of an objective. When there are multiple objectives to choose from, what is needed is a system which may curate the medical features extracted from patient health information to a specific model associated with the prediction of the desired objective. One relevant objective is to compute the likelihood that a patient's fractional flow reserve indicates a degree of stenosis within a defined period of time after one or more events, such as receiving an electrocardiogram.

SUMMARY

In some embodiments, systems and methods are provided for generating, training, and applying models for predicting an objective based on features associated with a patient. The model(s) can be selected based on amount, type, and other properties of information available for a patient. The systems and methods provide techniques for computational processing of information in patient records (e.g., various semi-structured and unstructured data) to convert the information into a format suitable for use in the predictive models. Thus, in some embodiments, interactions are identified in a patient record, and, for every identified interaction, a prediction of an objective may be calculated. The prediction can relate to, for example, a likelihood that a patient's fractional flow reserve (FFR) indicates a degree of stenosis within a defined period of time after one or more events, such as receiving an electrocardiogram. The predictions are identified using a model that can be selected from a plurality of models based on the available patient information.

In accordance with an example, a method includes: receiving, to one or more processors, electrocardiogram signal data for a patient; receiving, to the one or more processors, observational patient feature data for the patient; applying, in the one or more processors, the electrocardiogram signal data and the observational patient feature data to a trained machine learning engine, wherein the machine learning engine includes one or more cardiac objective models and trained using a training electrocardiogram signal data set and a training observational patient feature data set, to predict a cardiac objective state; and predicting, in the one or more processors, a probability of the cardiac objective state using the trained machine learning model.

In some examples, the trained machine learning engine includes at least one of an atrial fibrillation model, a hemodynamic alteration model, and a fractional flow reserve (FFR) model.

In some examples, the method further includes: in response to predicting the probability of the cardiac objective state, predicting, in the one or more processors, a target cardiac outcome.

In some examples, the trained machine learning engine includes an atrial fibrillation model, and wherein the target cardiac outcome includes at least one of a previous cardiac event, a current cardiac event, or a future cardiac event.

In some examples, the target cardiac outcome includes at least one of a previous heart attack, a current heart attack, or a predicted future heart attack.

In some examples, the trained machine learning engine includes a hemodynamic alteration model, and wherein the target cardiac outcome includes at least one of hypertension, myocardial infarctions, or an embolism.

In some examples, the trained machine learning engine includes a FFR model, and wherein the target cardiac outcome includes at least one of FFR abnormalities, stenosis, coronary disease, heart attack, or irregular heartbeat.

In some examples, the method further includes: in response to predicting the probability of the cardiac objective state, predicting, in the one or more processors, a time window of a future target cardiac outcome, a time window since a previous cardiac outcome, or a time window of a current cardiac outcome.

In some examples, the trained machine learning engine includes at least one of a disease progression model or a disease recurrence model.

In some examples, the electrocardiogram signal data includes short lead electrocardiogram signal data and/or long lead electrocardiogram signal data.

In some examples, the short lead electrocardiogram signal data includes 1250 signal values per short lead and the long lead electrocardiogram signal data includes 5000 signal values per long lead.

In some examples, the observational patient feature data includes patient gender data and patient age data.

In some examples, the observational patient feature data includes RNA feature data or DNA feature data.

In some examples, the observational patient feature data includes image feature data.

In some examples, the image feature data includes IHC slide image data or H&E slide image data.

In some examples, the IHC slide image data or H&E slide image data includes one or more of programmed death-ligand 1 (PD-L1) status, human leukocyte antigen (HLA) status, or immunology-related features.

In some examples, the observational patient feature data includes genetic variants data determined for gene sequencing data of a sample.

In some examples, the observational patient feature data includes genetic variants data that identifies single or multiple nucleotide polymorphisms, identifies whether a variation is an insertion or deletion event, identifies loss or gain of function, identifies fusions, is copy number variation data, is microsatellite instability data, or is structural variations within the DNA or RNA data.

In some examples, the observational patient feature data includes data indicating one or more of diagnosis, symptoms, therapies, outcomes, patient demographics such as patient name, date of birth, gender, ethnicity, date of death, address, smoking status, diagnosis dates for heart disease, stenosis, atrial fibrillation, hemodynamic alteration, coronary artery disease, cancer, illness, disease, diabetes, depression, other physical or mental maladies, personal medical history, family medical history, clinical diagnoses such as date of initial diagnosis, treatments and outcomes such as line of therapy, therapy groups, clinical trials, medications prescribed or taken, surgeries, radiotherapy, imaging, adverse effects, associated outcomes, genetic testing and laboratory information such as performance scores, lab tests, pathology results, prognostic indicators, date of genetic testing, testing provider used, testing method used, such as genetic sequencing method or gene panel, gene results, such as included genes, variants, expression levels/statuses, or corresponding dates associated thereof.

In some examples, the observational patient feature data includes proteomic data, transcriptome data, epigenomic data, metabolomics data, or microbiome data.

In some examples, the observational patient feature data includes organoid derived data.

In some examples, the observational patient feature data includes data indicating patient symptoms, diagnosis, treatments, medications, therapies, hospice, responses to treatments, laboratory testing results, medical history, geographic locations of each, demographics, or other features of the patient which may be found in the patient's medical record.

In some examples, the observational patient feature data includes proteomic data, transcriptome data, epigenomic data, metabolomics data, or microbiome data.

In some examples, the trained machine learning engine is configured of one or more gradient boosting models, one or more random forest models, one or more convolution neural networks (CNNs), one or more neural networks (NN), one or more regression models, one or more Naive Bayes models, or one or more machine learning algorithms (MLA).

In some examples, the trained machine learning engine is a CNN comprising a plurality of 1D convolutional blocks receiving the electrocardiogram signal data.

In some examples, the trained machine learning engine is a CNN includes a first branch of 1D convolutional blocks for receiving short lead electrocardiogram signal data and a second branch of 1D convolutional blocks for receiving long lead electrocardiogram signal data.

In some examples, the CNN includes a fully connected convolutional layer connected to an output of the first branch and an output of the second branch and connected to an output node with a softmax function layer for generating the probability of the cardiac objective state.

In some examples, applying the electrocardiogram signal data and the observational patient feature data to the trained machine learning engine includes: applying the electrocardiogram signal data to the plurality of 1D convolutional blocks and applying the observational patient feature data to the softmax function layer.

In some examples, the trained machine learning engine is a CNN includes a first branch of 1D convolutional blocks for receiving short lead electrocardiogram signal data, a second branch of 1D convolutional blocks for receiving long lead electrocardiogram signal data, a third branch of 1D convolutional blocks for receiving the observational patient feature data, and a fully connected convolutional layer connected to each branch connected to an output node with a softmax function layer for generating the probability of the cardiac objective state.

In some examples, receiving the electrocardiogram signal data includes receiving the electrocardiogram signal data from an electrocardiogram apparatus over a communication network.

In some examples, the communication network is a wireless network.

In some examples, the communication network is a wired network.

In some examples, the one or more processors are located in a cloud-based server, and wherein receiving the electrocardiogram signal data includes receiving the electrocardiogram signal data from an electrocardiogram apparatus communicatively coupled to the cloud-based server via a cloud network.

In accordance with another example, an electrocardiogram apparatus configured to perform any of the foregoing methods.

In some examples, the electrocardiogram apparatus comprises a plurality of electrocardiogram leads for collecting the electrocardiogram signal data.

In some examples, the electrocardiogram apparatus is a portable apparatus.

In some examples, the electrocardiogram apparatus is a fixed or mounted apparatus.

In accordance with another example, a cloud-based server is configured to perform any of the foregoing methods.

In accordance with another example, a microservice stored on a computer readable medium of a computing device having the one or more processors, the microservice being executable on the computing device to perform the any of the foregoing methods.

In some examples, the computing device is a digital and laboratory health care platform.

In some examples, the computing device is an order management system.

In some examples, receiving the electrocardiogram signal data includes receiving the electrocardiogram signal data from a plurality of electrocardiogram leads.

In some examples, receiving the electrocardiogram signal data includes receiving the electrocardiogram signal data in a data file, as image data, or in a digital or printed document.

In some examples, the receiving the observational patient feature data includes receiving the observational patient feature data from an electronic medical record (EMR), a pathology report, radiology report, and/or molecular data report.

In some examples, the method further includes: in response to predicting the probability of the cardiac objective state, predicting, in the one or more processors, a target cardiac outcome; and automatically generating an electronic report including the predictions of probability of the target cardiac outcome.

In some examples, the method further includes: transmitting the electronic report to a user over a computer network in real time, so that the user has immediate access to the electronic report.

In some examples, the electronic report is generated as part of a precision medicine result delivery for the patient.

In some examples, the electronic report includes a recommendation to a physician to treat the patient using a treatment that correlates with the target cardiac outcome.

In some examples, the electronic report includes a recommendation to a physician to select a treatment which provides adjustments to a typical monitoring including one or more of scanning, imaging, and blood testing.

In some examples, the method further includes: displaying, at least in part, the predictions on a graphical user interface of a computing device.

In some examples, the predictions are displayed on the graphical user interface in association with information one or more observational patient features.

In some examples, the method further includes: receiving, via the graphical user interface, a request to display ranking information associated with the one or more observational patient features, the ranking information comprising a score associated with each feature of the one or more observational patient features.

In some examples, wherein the request includes a threshold for scores associated with the features of the one or more observational patient features, and wherein the method includes displaying the information on the one or more observational patient features based on the threshold.

BRIEF DESCRIPTION OF THE DRAWINGS

The figures described below depict various aspects of the system and methods disclosed herein. It should be understood that each figure depicts an example of aspects of the present systems and methods.

DETAILED DESCRIPTION

Figure 1:
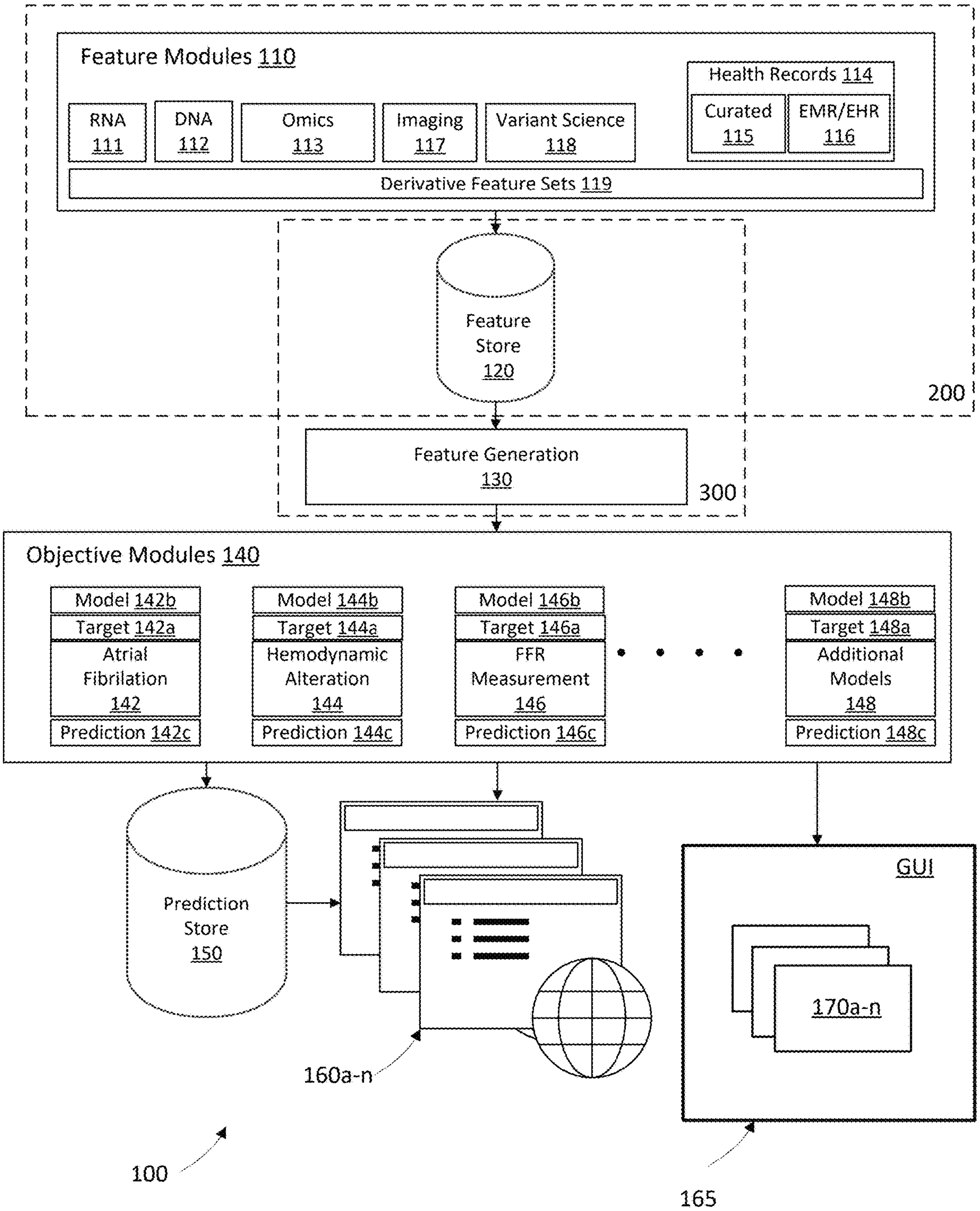
FIG. 1 is a block diagram illustrating a system for generating predictions of an objective from a plurality of patient features, in accordance with some embodiments of the present disclosure.

FIG. 1 illustrates an embodiment of a computer-implemented system 100 for generating and modeling predictions of patient objectives. Predictions may be generated from patient information represented by feature modules 110 implemented by the system architecture 100. The system 100 can be a content server (also referred to as a prediction engine), which is hardware or a combination of both hardware and software. A user, such as a health care provider or patient, is given remote access through the GUI to view, update, and analyze information about a patient's medical condition using the user's own local device (e.g., a personal computer or wireless handheld device). A user can interact with the system to instruct it to generate electronic records, update the electronic records, and perform other actions. The content server is configured to receive various information in different formats and it converts the information into the standardized format that is suitable for processing by modules operation on or in conjunction with the content server. Thus, information acquired from patients' electronic medical records (EMR), unstructured text, genetic sequencing, imaging, and various other information can be converted into features that are used for training a plurality of machine-learning models.

The information acquired, processed, and generated by the content server 100 is stored on one or more of the network-based storage devices. The user can interact with the content server to access the information stored in the network-based storage devices, and the content server can receive user-supplied information, apply the one or more models stored in the network-based storage to the information, and provide, in an electronic form, results of the model application to the user on a graphical user interface of the user device. The electronic information is transmitted in a standardized format over the computer network to the users that have access to the information. In this way, the users can readily adapt their medical diagnostic and treatment strategy in accordance with the system's predictions which can be automatically generated. Moreover, the system generates recommendations to users regarding patient diagnosis and treatment.

In some embodiments, the described systems and methods are implemented as part of a digital and laboratory health care platform. The platform may automatically generate an electrocardiogram report or molecular report as part of a targeted medical care precision medicine treatment. In some embodiments, the system in accordance with embodiments of the present disclosure operates on one or more microservices, which can be microservices of an order management system. In some embodiments, the system is implemented in conjunction with one or more microservices of a medical profiling service.

The feature modules 110 may store a collection of features, or status characteristics, generated for some or all patients whose information is present in the system 100. These features may be used to generate and model predictions using the system 100. While feature scope across all patients is informationally dense, a patient's feature set may be sparsely populated across the entirety of the collective feature scope of all features across all patients. For example, the feature scope across all patients may expand into the tens of thousands of features, while a patient's unique feature set may include a subset of hundreds or thousands of the collective feature scope based upon the records available for that patient.

A plurality of features present in the feature modules 110 may include a diverse set of fields available within patient health records 114. Clinical information may be based upon fields which have been entered into an electronic medical record (EMR) or an electronic health record (EHR) 116, which can be done automatically or manually, e.g., by a physician, nurse, or other medical professional or representative. Other clinical information may be curated information (115) obtained from other sources, such as, for example, genetic sequencing reports (e.g., from molecular fields). Sequencing may include next-generation sequencing (NGS) and may be long-read, short-read, or other forms of sequencing a patient's genome. A comprehensive collection of features (status characteristics) in additional feature modules may combine a variety of features together across varying fields of medicine which may include diagnoses, responses to treatment regimens, genetic profiles, clinical and phenotypic characteristics, and/or other medical, geographic, demographic, clinical, molecular, or genetic features. For example, as shown in FIG. 1, a subset of features may comprise molecular data features, such as features derived from an RNA feature module 111 or a DNA feature module 112 sequencing.

As further shown in FIG. 1, another subset of features, imaging features from imaging feature module 117, may comprise features identified via resting 12-lead electrocardiograms (ECGs) such as 1250 signal values short leads (e.g., Leads I, V2, V3, V4, V6) or 5000 signal values per long, rhythm ECG lead (e.g., Leads II, V1, V5), fractional flow reserve measurements between 0-1. Other image features may include those identified, for example, through review of a specimen by pathologist, such as, e.g., a review of stained H&E or IHC slides. As another example, a subset of features may comprise derivative features obtained from the analysis of the individual and combined results of such feature sets. Features derived from DNA and RNA sequencing may include genetic variants from variant science module 118, which can be identified in a sequenced sample. Further analysis of the genetic variants present in variant science module 118 may include steps such as identifying single or multiple nucleotide polymorphisms, identifying whether a variation is an insertion or deletion event, identifying loss or gain of function, identifying fusions, calculating copy number variation, calculating microsatellite instability, or other structural variations within the DNA and RNA. Analysis of slides for H&E staining or IHC staining may reveal features such as programmed death-ligand 1 (PD-L1) status, human leukocyte antigen (HLA) status, or other immunology-related features.

Features derived from structured, curated, and/or electronic medical or health records 114 may include clinical features such as diagnosis, symptoms, therapies, outcomes, patient demographics such as patient name, date of birth, gender, ethnicity, date of death, address, smoking status, diagnosis dates for heart disease, stenosis, atrial fibrillation, hemodynamic alteration, coronary artery disease, cancer, illness, disease, diabetes, depression, other physical or mental maladies, personal medical history, family medical history, clinical diagnoses such as date of initial diagnosis, treatments and outcomes such as line of therapy, therapy groups, clinical trials, medications prescribed or taken, surgeries, radiotherapy, imaging, adverse effects, associated outcomes, genetic testing and laboratory information such as performance scores, lab tests, pathology results, prognostic indicators, date of genetic testing, testing provider used, testing method used, such as genetic sequencing method or gene panel, gene results, such as included genes, variants, expression levels/statuses, or corresponding dates associated with any of the above.

As shown in FIG. 1, the features 113 may be derived from information from additional medical- or research-based Omics fields including proteome, transcriptome, epigenome, metabolome, microbiome, and other multi-omic fields. Features derived from an organoid modeling lab may include the DNA and RNA sequencing information germane to each organoid and results from treatments applied to those organoids. Features 117 derived from imaging data may further include reports associated with a stained slide, as well as machine learning approaches for classifying PDL1 status, HLA status, or other characteristics from imaging data. Other features may include additional derivative features sets 119 derived using other machine learning approaches based at least in part on combinations of any new features and/or those listed above. For example, imaging results may need to be combined with MSI calculations derived from RNA expressions to determine additional further imaging features. As another example, a machine-learning model may generate a likelihood that a patient's fractional flow reserve indicates a degree of stenosis within a defined period of time after an electrocardiogram. Additional derivative feature sets are discussed in more detail below with respect to FIG. 2. Other features that may be extracted from medical information may also be used. There are many thousands of features, and the above-described types of features are merely representative and should not be construed as a complete listing of features.

In addition to the above features and enumerated modules, the feature modules 110 may further include one or more of the modules that are described below and that can be included within respective modules of the Feature modules 110, as a sub-module or as a stand-alone module.

Continuing with FIG. 1, a DNA feature module 112 may comprise a feature collection associated with the DNA-derived information of a patient. These features may include raw sequencing results, such as those stored in FASTQ, BAM, VCF, or other sequencing file types known in the art; genes; mutations; variant calls; and variant characterizations. Genomic information from a patient's sample may be stored.

An RNA feature module 111 may comprise a feature collection associated with the RNA-derived information of a patient, such as transcriptome information. These features may include, for example, raw sequencing results, transcriptome expressions, genes, mutations, variant calls, and variant characterizations. Features may also include normalized sequencing results, such as those normalized for unit variance.

The feature modules 110 can comprise various other modules. For example, a metadata module (not shown) may comprise a feature collection associated with the standard ECG results, human genome, protein structures and their effects, such as changes in energy stability based on a protein structure.

A clinical module (not shown) may comprise a feature collection associated with information derived from clinical records of a patient, which can include records from family members of the patient. These may be abstracted from unstructured clinical documents, EMR, EHR, or other sources of patient history. Information may include patient symptoms, diagnosis, treatments, medications, therapies, hospice, responses to treatments, laboratory testing results, medical history, geographic locations of each, demographics, or other features of the patient which may be found in the patient's medical record. Information about treatments, medications, therapies, and the like may be ingested as a recommendation or prescription and/or as a confirmation that such treatments, medications, therapies, and the like were administered or taken.

An imaging module, such as, e.g., the imaging module 117, may comprise a feature collection associated with information derived from imaging records of a patient. Imaging records may include electrocardiograms, fractional flow reserve, H&E slides, IHC slides, radiology images, and other medical imaging information, as well as related information from pathology and radiology reports, which may be ordered by a physician during the course of diagnosis and treatment of various illnesses and diseases. These features may include ECG features of waves, intervals, segments and one complex. Wave: A positive or negative deflection from baseline that indicates a specific electrical event. The waves on an ECG include the P wave, Q wave, R wave, S wave, T wave and U wave. Interval: The time between two specific ECG events. The intervals commonly measured on an ECG include the PR interval, QRS interval (also called QRS duration), QT interval and RR interval. Segment: The length between two specific points on an ECG that are supposed to be at the baseline amplitude (not negative or positive). The segments on an ECG include the PR segment, ST segment and TP segment. Complex: The combination of multiple waves grouped together. The only main complex on an ECG is the QRS complex. Point: There is only one point on an ECG termed the J point, which is where the QRS complex ends and the ST segment begins. The main part of an ECG typically contains a P wave, QRS complex and T wave.

The P wave indicates atrial depolarization. The QRS complex consists of a Q wave, R wave and S wave and represents ventricular depolarization. The T wave comes after the QRS complex and indicates ventricular repolarization. Standard 12-lead ECG may include a 10-second strip. The bottom one or two lines will be a full "rhythm strip" of a specific lead, spanning the whole 10 seconds of the ECG. Other leads may be shorter and span only 2.5 seconds.

The TP segment is the portion of the ECG from the end of the T wave to the beginning of the P wave. This segment may show baseline for a patient and may be used as a reference to determine whether the ST segment is elevated or depressed, as there are no specific disease conditions that elevate or depress the TP segment.

During states of tachycardia, the TP segment is shortened and may be difficult to visualize altogether. The TP segment my show the presence of U waves or atrial activity that could indicate pathology.

Additional imaging features from ECG may include identifications of disease states and conditions for atrial arrhythmias, chamber enlargements, conduction abnormalities, ischemic heart disease, ventricular arrythmias, and other ECG related features.

Additional imaging features may include nuclear-cytoplasmic ratio, large nuclei, cell state alterations, biological pathway activations, hormone receptor alterations, immune cell infiltration, immune biomarkers of MMR, MSI, PDL1, CD3, FOXP3, HRD, PTEN, PIK3CA; collagen or stroma composition, appearance, density, or characteristics; chromatin morphology; and other characteristics of cells or tissues for prognostic predictions.

An epigenome module, such as, e.g., an epigenome module from Omics module 113, may comprise a feature collection associated with information derived from DNA modifications which are not changes to the DNA sequence and regulate the gene expression. These modifications can be a result of environmental factors based on what the patient may breathe, eat, or drink. These features may include DNA methylation, histone modification, or other factors which deactivate a gene or cause alterations to gene function without altering the sequence of nucleotides in the gene.

A microbiome module, such as, e.g., a microbiome module from Omics module 113, may comprise a feature collection associated with information derived from the viruses and bacteria of a patient. These features may include viral infections which may affect treatment and diagnosis of certain illnesses as well as the bacteria present in the patient's gastrointestinal tract which may affect the efficacy of medicines ingested by the patient.

A proteome module, such as, e.g., a proteome module from Omics module 113, may comprise a feature collection associated with information derived from the proteins produced in the patient. These features may include protein composition, structure, and activity; when and where proteins are expressed; rates of protein production, degradation, and steady-state abundance; how proteins are modified, for example, post-translational modifications such as phosphorylation; the movement of proteins between subcellular compartments; the involvement of proteins in metabolic pathways; how proteins interact with one another; or modifications to the protein after translation from the RNA such as phosphorylation, ubiquitination, methylation, acetylation, glycosylation, oxidation, or nitrosylation.

Additional Omics module(s) (not shown) may also be included in Omics module 113, such as a feature collection (which is a collection of status characteristics) associated with all the different field of omics, including: cognitive genomics, a collection of features comprising the study of the changes in cognitive processes associated with genetic profiles; comparative genomics, a collection of features comprising the study of the relationship of genome structure and function across different biological species or strains;

functional genomics, a collection of features comprising the study of gene and protein functions and interactions including transcriptomics; interactomics, a collection of features comprising the study relating to large-scale analyses of gene-gene, protein-protein, or protein-ligand interactions; metagenomics, a collection of features comprising the study of metagenomes such as genetic material recovered directly from environmental samples; neurogenomics, a collection of features comprising the study of genetic influences on the development and function of the nervous system; pangenomics, a collection of features comprising the study of the entire collection of gene families found within a given species; personal genomics, a collection of features comprising the study of genomics concerned with the sequencing and analysis of the genome of an individual such that once the genotypes are known, the individual's genotype can be compared with the published literature to determine likelihood of trait expression and disease risk to enhance personalized medicine suggestions; epigenomics, a collection of features comprising the study of supporting the structure of genome, including protein and RNA binders, alternative DNA structures, and chemical modifications on DNA; nucleomics, a collection of features comprising the study of the complete set of genomic components which form the cell nucleus as a complex, dynamic biological system; lipidomics, a collection of features comprising the study of cellular lipids, including the modifications made to any particular set of lipids produced by a patient; proteomics, a collection of features comprising the study of proteins, including the modifications made to any particular set of proteins produced by a patient; immunoproteomics, a collection of features comprising the study of large sets of proteins involved in the immune response; nutriproteomics, a collection of features comprising the study of identifying molecular targets of nutritive and non-nutritive components of the diet including the use of proteomics mass spectrometry data for protein expression studies; proteogenomics, a collection of features comprising the study of biological research at the intersection of proteomics and genomics including data which identifies gene annotations; structural genomics, a collection of features comprising the study of 3-dimensional structure of every protein encoded by a given genome using a combination of modeling approaches; glycomics, a collection of features comprising the study of sugars and carbohydrates and their effects in the patient; foodomics, a collection of features comprising the study of the intersection between the food and nutrition domains through the application and integration of technologies to improve consumer's well-being, health, and knowledge; transcriptomics, a collection of features comprising the study of RNA molecules, including mRNA, rRNA, tRNA, and other non-coding RNA, produced in cells; metabolomics, a collection of features comprising the study of chemical processes involving metabolites, or unique chemical fingerprints that specific cellular processes leave behind, and their small-molecule metabolite profiles; metabonomics, a collection of features comprising the study of the quantitative measurement of the dynamic multiparametric metabolic response of cells to pathophysiological stimuli or genetic modification; nutrigenetics, a collection of features comprising the study of genetic variations on the interaction between diet and health with implications to susceptible subgroups; cognitive genomics, a collection of features comprising the study of the changes in cognitive processes associated with genetic profiles; pharmacogenomics, a collection of features comprising the study of the effect of the sum of variations within the human genome on drugs; pharmacomicrobiomics, a collection of features comprising the study of the effect of variations within the human microbiome on drugs; toxicogenomics, a collection of features comprising the study of gene and protein activity within particular cell or tissue of an organism in response to toxic substances; mitointeractome, a collection of features comprising the study of the process by which the mitochondria proteins interact; psychogenomics, a collection of features comprising the study of the process of applying the powerful tools of genomics and proteomics to achieve a better understanding of the biological substrates of normal behavior and of diseases of the brain that manifest themselves as behavioral abnormalities, including applying psychogenomics to the study of drug addiction to develop more effective treatments for these disorders as well as objective diagnostic tools, preventive measures, and cures; stem cell genomics, a collection of features comprising the study of stem cell biology to establish stem cells as a model system for understanding human biology and disease states; connectomics, a collection of features comprising the study of the neural connections in the brain; microbiomics, a collection of features comprising the study of the genomes of the communities of microorganisms that live in the digestive tract; cellomics, a collection of features comprising the study of the quantitative cell analysis and study using bioimaging methods and bioinformatics; tomomics, a collection of features comprising the study of tomography and omics methods to understand tissue or cell biochemistry at high spatial resolution from imaging mass spectrometry data; ethomics, a collection of features comprising the study of high-throughput machine measurement of patient behavior; and videomics, a collection of features comprising the study of a video analysis paradigm inspired by genomics principles, where a continuous digital image sequence, or a video, can be interpreted as the capture of a single image evolving through time of mutations revealing patient insights.

In some embodiments, a robust collection of features may include all of the features disclosed above. However, predictions based on the available features may include models which are optimized and trained from a selection of fewer features than in an exhaustive feature set. Such a constrained feature set may include, in some embodiments, from tens to hundreds of features. For example, a prediction may include predicting the likelihood that a patient's fractional flow reserve indicates a degree of stenosis within a defined period of time after an electrocardiogram. A model's constrained feature set may include the ECG results from a 12-lead, resting ECG, a stress or exercise ECG, an ambulatory ECG, or an ECG having a differing number of leads selected from the limb leads (six limb leads are called lead I, II, III, aVL, aVR and aVF) or precordial leads (six precordial leads are called leads V1, V2, V3, V4, V5 and V6) in addition to the patient's age, gender, RNA or DNA sequencing results, or other clinical features. Examples of optimized feature sets are further discussed below, in connection with FIGS. 3-5.

The feature store 120 may enhance a patient's feature set through the application of machine learning and/or an artificial intelligence engine and analytics by selecting from any features, alterations, or calculated output derived from the patient's features or alterations to those features. One method for enhancing a patient's feature set may include dimensionality reduction, such as collapsing a feature set from tens of thousands of features to a handful of features. Performing dimensionality reduction without losing information may be approached in an unsupervised manner or a supervised manner. Unsupervised methods may include RNA Variational Auto-encoders, Singular Value Decomposition (SVD), PCA, KernelPCA, SparsePCA, DictionaryLearning, Isomap, Nonnegative Matrix Factorization (NMF), Uniform Manifold Approximation and Projection (UMAP), Feature agglomeration, Patient correlation clustering, KMeans, Gaussian Mixture, or Spherical KMeans. Performing dimensionality reduction in a supervised manner may include Linear Discriminant Analysis, Neighborhood Component Analysis, MLP transfer learning, or tree based supervised embedding.

In one embodiment, a convolutional neural network (CNN) may receive each lead of an ECG at a one dimensional convolutional layer and each branch may be received at a fully connected layer before being supplied to a sigmoid function (or softmax function) for generating prediction results, such as a raw FFR measurement or the likelihood of a patient's FFR measurement indicating stenosis.

In one embodiment, a grid search may be performed across a variety of encoding, such as the supervised and unsupervised approaches above, where each encoding is evaluated across a variety of hypertuning parameters to identify the encoding and hyperparameter set which generates the highest dimensionality reduction while retaining or improving accuracy.

In one embodiment, a grid search may identify a dimensionality reduction implemented with tree-based supervised embedding on RNA TPM feature sets for all patients. RNA TPM feature sets may be fit to a forest of decision trees, such as a forest of decision trees generated from hyperparameters of minimum samples per leaf using a minimum number of 2, 4, 8, 16, 24, 100, or other selected number, a maximum feature set using a percentage of the features which should be used in each tree, the number of trees to be used in the forest, and the number of clusters which may be identified from the reduced dimensionality data set. Each tree in the forest may randomly select up to the threshold percentage of features and with each selected feature identify the largest split between patients who have a disease state diagnosis and those who do not. When the feature set includes RNA TPM features, a random selection of genes may include identifying which genes are the most divisive of the random set of selected features, starting the branching from the most divisive gene and successively iterating down the gene list until either the minimum samples per leaf are not met or the maximum features are met. The leaf nodes for each tree include patients who meet the criteria at each branch and are correlated based upon their likelihood to develop the disease state. Patient membership of each leaf may be evaluated using one-hot KMeans cluster membership counts or a distance of each patient to each of the KMeans centroids/clusters.

In an example, the leaves of each tree are compared to identify which leaves include the same branches or equivalent branches, such as branches that result in the same patients because the genes, while different, are equivalent to each other. Equivalency may be determined when information related to the expression level of a gene may be correlated with, or predicted from, the expression level data associated with one or more other genes. When a gene may be correlated with, or predicted from, one or more other genes, the one or more other genes are defined as proxy genes. The terms proxy genes and equivalent genes may be used interchangeably herein. Identifying the number of same branches, or equivalent branches, for each leaf allows generation of membership for each leaf as it occurs within the individual trees of the forest. Similarly, when KMeans clusters are generated from the collection of leafs, a distance for each patient may be calculated for each patient. An array may be generated having the normalized inverse of each distance for each patient to each KMeans centroid. The array, at this point, may be stored as a reduced dimensionality feature set of RNA TPM features for the set of patients, and the features of reduced dimensionality may be used in any of the predictive methods described herein. In other words, the methods for identifying a prediction of a target/objective pair may be performed having the array of distances for each patient as an input into the artificial intelligence engine described below; including, for example, performing logistic regression to generate a predictive model for a target/objective pair.

The feature store 120 may generate new features from the original features found in feature module 110 or may identify and store insights or analysis derived using the features. The selections of features may be based upon an alteration or calculation to be generated and may include ECG features such as the ECG imaging features above, hypertension, myocardial infarction, or other signatures of irregular heartbeats. The selections of features may also include the calculation of single or multiple nucleotide polymorphisms, insertion or deletions of the genome, a microsatellite instability, a copy number variation, a fusion, or other such calculations. In an example, an output of an alteration module which may inform future alterations or calculations may include a finding that patients having hypertrophic cardiomyopathy (HCM) express variants in MYH7 more commonly than patients without HCM. An exemplary approach may include the enrichment of variants and their respective classifications to identify a region in MYH7 that is associated with HCM. Any novel variants detected from patient's sequencing localized to this region would increase the patient's risk for HCM. Therefore, features which may be utilized in such an alteration detection include the structure of MYH7, the normal genome for MYH7, and classification of variants therein as impacting a patient's chances of having HCM. A model which focuses on enrichment may isolate such variants. Other variants may be isolated with respect to other illness, diseases, or diagnosis through an enrichment alteration module. The feature store selection, alteration, and calculations are discussed below in more detail with respect to FIG. 2.

The feature generation 130 may process features from the feature store 120 by selecting or receiving features from the feature store 120. The features may be selected based on a patient by patient basis, a target/objective by patient basis, or a target/objective by all patient basis, or a target/objective by cohort basis. In the patient by patient basis, features which occur a specified patient's timeline of medical history may be processed. In the target/objective by patient basis, features which occur in a specified patient's timeline which inform an identified target/objective prediction may be processed. In some examples, a model may be selected which optimizes the prediction based upon the features available to the prediction engine at the time of processing/generating a prediction for the patient or a prediction for all of the patients.

Targets/objectives may include a combination of an objective and a horizon, or time period, such as atrial fibrillation, hemodynamic alteration, heart disease within 1, 3, 6, 12 months, FFR measurement within 1 day, Progression within 6, 12, 24, 60 months, Death within 6, 12, 24, 60 months; Recurrence within 6, 12, 24, 60 months; First Administration of Medication within 7, 14, 21, or 28 days; First Occurrence of Procedure within 7, 14, 21, or 28 days; or First Occurrence of Adverse Reaction within 6, 12, or 24 months of Initial Administration. The above listing of targets/objectives is not exhaustive, other objectives and horizons may be used based upon the predictions requested from the system. In one example, the prediction may be represented as P(Y(t) X), where P is the probability of developing a heart attack Y at time t given a patient's current medical state and history X. Where the P includes a target/objective, the X includes the patient features in the system. In the target/objective by all-patient basis, features which occur in each patient's timeline which inform an identified target/objective prediction may be processed for each patient until all patients have been processed. In the target/objective by cohort basis, features which occur in each patient's timeline which inform an identified target prediction may be processed for each patient until all patients of a cohort have been processed. A cohort may include a subset of patients having attributes in common with each other. For example, a cohort may be a collection of patients which share a common institution (such as a hospital or clinic), a common diagnosis (such as arrhythmias, heart disease, irregular heartbeats, heart attack, cancer, depression, or other illness), a common treatment (such as a medication or therapy), common molecular characteristics (such as a genetic variation or alteration), or laboratory measurements (such as an FFR measurement, heart testing results, or blood testing results). Cohorts may be derived from any feature or characteristic included in the feature modules 110 or feature store 120. Feature generation may provide a prior feature set and/or a forward feature set to a respective objective module corresponding to the target/objective and/or prediction to be generated. Prior and forward feature sets will be disclosed in more detail with respect to FIGS. 3-5, below.

Objective Modules 140 may comprise a plurality of modules: Atrial Fibrillation 142, Hemodynamic Alteration 144, FFR Measurement 146, and further additional models 148 which may include modules such as Medication or Treatment prediction, Adverse Response prediction, disease progression, disease recurrence, poor contact tracing classifiers, stenosis classifiers, coronary artery disease classifiers, arrhythmia classifiers, irregular heartbeat classifiers, or other predictive models. Each module 142, 144, 146, and 148 may be associated with one or more targets 142*a*, 144*a*, 146*a*, and 148*a*, which may be target cardiac outcomes. For example, atrial fibrillation module 142 may be associated with targets 142*a* having the objective 'previous heart attack, current heart attack, or future heart attack' and time periods '−12, −6, 0, 1, 3, 6, and 12 months.' Hemodynamic Alteration module 144 may be associated with targets 144*a* having the objective 'hypertension, myocardial infarctions, or embolism' and time periods '−12, −6, 0, 1, 3, 6, and 12 months.' FFR Measurement module 146 may be associated with targets 146*a* having the objective Stenosis, Coronary Disease, Heart Attack' and time periods '−12, −6, 0, 1, 3, 6, and 12 months.' Additional models 148, such as a Propensity Module may be associated with targets 148*a* having an objective 'Medications, Treatments, and Therapies' and time periods '7, 14, 21, and 28 days.' Additional models 148, such as a poor contact tracing classifiers (objective 'contact quality', target 'at time of ECG'), stenosis classifiers, coronary artery disease classifiers, arrhythmia classifiers, irregular heartbeat classifiers may identify objectives of 'previous occurrence, current state, or future state' for each respective classification for time periods '−12, −6, 0, 1, 3, 6, and 12 months.' Other additional models such as Disease Progression Module and Disease Recurrence Module may be associated with targets 148*a* having an objective 'Progression, Recurrence' and time periods '6, 12, 24, and 60 months.'

Each module 142, 144, 146, and 148 may be further associated with models 142*b*, 144*b*, 146*b*, and 148*b*, for example, trained cardiac objective models (e.g., an atrial fibrillation model, a hemodynamic alteration model, an FFR model, etc.) each trained to predict a probability of a cardiac objective state such as the presence of atrial fibrillation, hemodynamic alteration, or FFR abnormalities, respectively, and target cardiac outcome. In the present application, "probability" is defined as including a binary value of 0, 1 and/or a distribution range between and including values 0-1. In various examples, a cardiac objective state may be a measure of cardiac performance, such as a measure of FFR or other metric, from which a target cardiac outcome may be determined or the cardiac objective state may be an actual target cardiac outcome. For example, model 146*b* may be a cardiac objective model trained to determine FFR and to further determine target outcomes such as at least one of FFR abnormalities, stenosis, coronary disease, heart attack, or irregular heartbeat. Model 144*b* may be a cardiac objective model trained to determine target cardiac outcomes such as hypertension, myocardial infarctions, or an embolism. Models 142*b*, 144*b*, 146*b*, and 148*b* may be gradient boosting models, random forest models, CNNs, neural networks (NN), regression models, Naive Bayes models, or machine learning algorithms (MLA). A MLA or a NN may be trained from a training data set such as a plurality of matrices having a feature vector for each patient or images and features. In an exemplary prediction profile, a training data set may include imaging, pathology, clinical, and/or molecular reports and details of a patient, such as those curated from an EHR or genetic sequencing reports. The training data may be based upon features such as the objective specific sets disclosed with respect to FIGS. 3-5, below.

MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, deep learning, long short term memory networks, or other neural models where the training data set includes a plurality of specimen samples, RNA expression data for each sample, and pathology reports covering imaging data for each sample. While MLA and neural networks identify distinct approaches to machine learning, the terms may be used interchangeably herein. Thus, a mention of MLA may include a corresponding NN or a mention of NN may include a corresponding MLA unless explicitly stated otherwise.

Training may include providing optimized datasets as a matrix of feature vectors for each patient, labeling these traits as they occur in patient records as supervisory signals, and training the MLA to predict an objective/target pairing. Artificial NNs are powerful computing models which have shown their strengths in solving hard problems in artificial intelligence. They have also been shown to be universal approximators (can represent a wide variety of functions when given appropriate parameters). Some MLA may identify features of importance and identify a coefficient, or weight, to them. The coefficient may be multiplied with the occurrence frequency of the feature to generate a score, and once the scores of one or more features exceed a threshold, certain classifications may be predicted by the MLA. A coefficient schema may be combined with a rule-based schema to generate more complicated predictions, such as predictions based upon multiple features. For example, ten key features may be identified across different classifications. A list of coefficients may exist for the key features, and a rule set may exist for the classification. A rule set may be based upon the number of occurrences of the feature, the scaled weights of the features, or other qualitative and quantitative assessments of features encoded in logic known to those of ordinary skill in the art.

In other MLAs, features may be organized in a binary tree structure. For example, key features which distinguish between the most classifications may exist as the root of the binary tree and each subsequent branch in the tree until a classification may be awarded based upon reaching a terminal node of the tree. For example, a binary tree may have a root node which tests for a first feature. The occurrence or non-occurrence of this feature must exist (the binary decision), and the logic may traverse the branch which is true for the item being classified. Additional rules may be based upon thresholds, ranges, or other qualitative and quantitative tests. While supervised methods are useful when the training dataset has many known values or annotations, the nature of EMR/EHR documents is that there may not be many annotations provided. When exploring large amounts of unlabeled data, unsupervised methods are useful for binning/bucketing instances in the data set. A single instance of the above models, or two or more such instances in combination, may constitute a model for the purposes of models 142*b*, 144*b*, 146, and 148*b*.

Models may also be duplicated for particular datasets which may be provided independently for each objective module 142, 144, 146, and 148. For example, the FFR Measurement objective module 146 may receive an ECG dataset, an ECG and clinical feature dataset, or a complete dataset comprising all features, including previous genetic sequencing results, for each patient. A model 146*b* may be generated for each of the potential feature sets or targets 146*a*. Each module 142, 144, 146, and 148 may be further associated with Predictions 142*c*, 144*c*, 146*c*, and 148*c*. A prediction may be a "probability" as used herein. As such, in various embodiments, a prediction may be a binary representation, such as a "Yes—Target predicted to occur" or "No—Target not predicted to occur." In various other embodiments, predictions may be a likelihood representation such as "target predicted to occur with 83% probability/likelihood." Predictions may be performed on patient data sets having known outcomes to identify insights and trends which are unexpected. For example, a cohort of patients may be generated for patients with a common history of heart disease who have either not had a heart attack for five years after a previous incident, have had multiple heart attacks within five years after a first heart attack, or who have passed away within five years of having their first heart attack. In other examples, a cohort of patients may be selected from any of the above referenced heart conditions, any time period in days, months, years, and any outcome. The cohort of patients may generate, for each event in a patient's medical file, the probability that the patient will not have a heart attack within the next two years and compare that prediction with whether the patient actually did not have a heart attack within two years of the event.

For example, a prediction that a patient may not have a heart attack with a 74% likelihood but in-fact does have one within two years may inform the prediction model that intervening events before the heart attack are worth reviewing or prompt further review of the patient record that lead to the prediction to identify characteristics which may further inform a prediction. An actual occurrence of a target is weighted to 1 and the non-occurrence of the event is weighted to 0, such that an event which is likely to occur but does not may be represented by the difference (0–0.73), an event which is not likely to occur but does may be represented by the difference (0.22–1), to provide a substantial difference in values in comparison to events which are closely predicted (0–0.12 or 1–0.89) having a minimal difference. Predictions will be discussed in further detail with respect to FIG. 6, below. For determining a prediction, each module 142, 144, 146, and 148 may be associated with a unique set of prior features, forward features, or a combination of prior features and forward features which may be received from feature generation 130. Selection of the unique set(s) of features will be disclosed in more detail with respect to FIGS. 3-5, below.

Prediction store 150 may receive predictions for targets/objectives generated from objective modules 140 and store them for use in the system 100. Predictions may be stored in a structured format for retrieval by a user interface such as, for example, a webform-based interactive user interface which, in some embodiments, may include webforms 160*a-n*. Webforms may support GUIs that can be displayed by a computer to a user of the computer system for performing a plurality of analytical functions, including initiating or viewing the instant predictions from objective modules 140 or initiating or adjusting the cohort of patients from which the objective modules 140 may perform analytics from. Electronic reports 170*a-n* may be generated and provided to the user via the graphical user interface (GUI) 165. It should be appreciated that the GUI 165 may be presented on a user device which is connected to the content server/prediction engine 100 via a network.

The reports 170 can be provided to the user as part of a network-based patient management system that collects, converts and consolidates patient information from various physicians and health-care providers (including labs) into a standardized format, stores it in network-based storage devices, and generates messages comprising electronic reports once the reports are generated in accordance with embodiments of the present disclosure. In this way, a user (e.g., a physician, oncologist, or any other health care provider, or a patient, receives computer-generated predictions related to a likelihood of a patient having stenosis, experiencing a heart attack, or developing a heart disease, the sections of the ECG which informed the predictions, and/or an associated timeline.

In some embodiments, the electronic report may include a recommendation to a physician to treat the patient using a treatment that correlates with a magnitude of a determined degree of risk, a recommendation to a physician to de-escalate when the patient is low risk to reduce adverse events, save cost and improve health response, or a recommendation to a physician to elect a treatment which provides adjustments to the typical monitoring such as scanning, imaging, blood testing. Additionally, or alternatively, the electronic report may include a recommendation for accelerated screening of the patient, a recommendation for consideration of additional monitoring. In some embodiments, an electronic report indicating that a patient may experience heart disease results in researchers planning a clinical trial by predicting which groups of patients are most likely to respond to therapy that targets heart disease in general or the occurrence of atrial fibrillation, hemodynamic alteration, stenosis, arrhythmias, an FFR Measurement above a threshold (e.g., 0.7, 0.8, 0.82, 0.9) or a specific heart disease of the prediction. In some embodiments, a clinical trial may be performed by selecting patients who are predicted to be more likely or less likely to develop the predicted heart disease, using systems and methods in accordance with the present disclosure.

Figure 2:
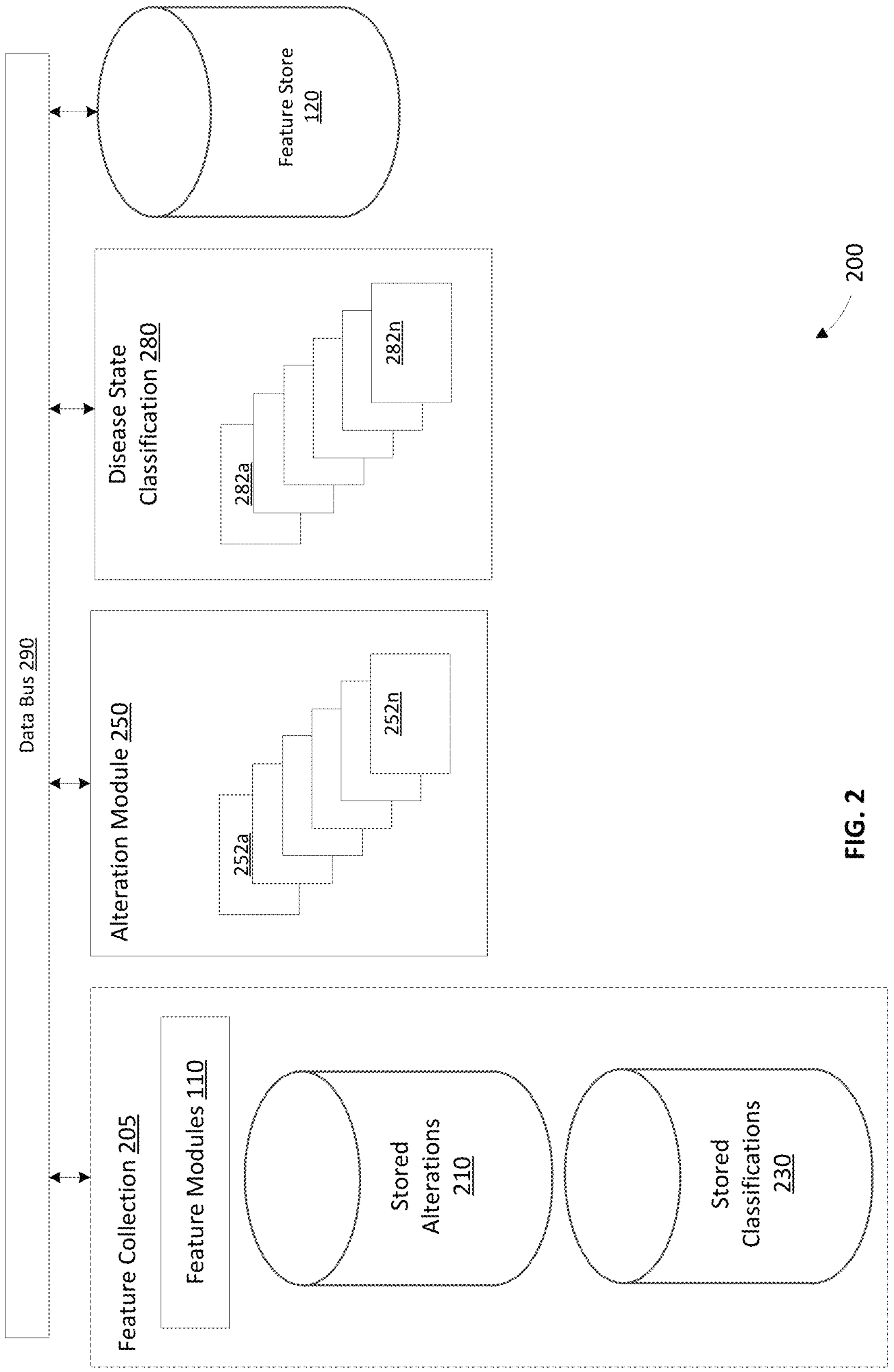
FIG. 2 is a block diagram illustrating a system for performing selection, alteration, and calculation of additional features from the patient features, in accordance with some embodiments of the present disclosure.
Figure 2A:
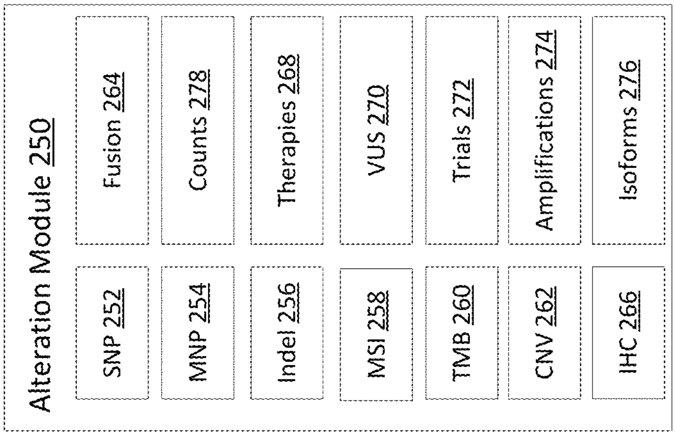
FIG. 2A is a block diagram illustrating on example of components within the alteration module of FIG. 2.

FIG. 2 illustrates the generation of additional derivative feature sets 119 of FIG. 1 and the feature store 120 using alteration modules. A feature collection 205 may comprise the modules of feature modules 110, stored alterations 210 from the alteration module 250 and stored classifications 230 from the disease state classification 280. An alteration module 250 may be one or more microservices, servers, scripts, or other executable algorithms 252*a-n* which generate alteration features associated with de-identified patient features from the feature collection. Exemplary alterations modules may include one or more of the following alterations as a collection of alteration modules 252*a-n*. As seen in FIG. 2A, within the alteration module 250, an SNP (single-nucleotide polymorphism) module 252 may identify a substitution of a single nucleotide that occurs at a specific position in the genome, where each variation is present to some appreciable degree within a population (e.g. >1%). For example, at a specific base position, or loci, in the human genome, the C nucleotide may appear in most individuals, but in a minority of individuals, the position is occupied by an A. This means that there is a SNP at this specific position and the two possible nucleotide variations, C or A, are said to be alleles for this position. SNPs underline differences in susceptibility to a wide range of diseases (e.g. —sickle-cell anemia, β-thalassemia and cystic fibrosis result from SNPs). Genes which can contribute to tumor formation because fusion genes can produce much more active abnormal protein than non-fusion genes. Some genes that may cause heart disease in various forms and cause receptor mediated endocytosis, recycling, reculation abnormalities, cholesterol absorption or excretion, high blood pressure, atrial or ventricle defects, aortic defects, or offer other contributing factors for development of heart diseases, atrial fibrillation, FFR, etc. includes: LDLR, APOB, ABCG5, ABCG8, ARH, PCSK9, ANGPTL3, SLC12A3, SLC12A1, KCNJ1, CLCNKB, NR3C2, SCNN1A, SCNN1B, SCNN1G, CYP11B2, CYP11B1, HSD11B2, NR3C2, SCNN1B, SCNN1G, WNK1, WNK4, KLHL3, CUL3, MYH7, TNNT2, TPM1, TNNI3, MYL2, MYBPC3, ACTC, MYL3, FBN1, NKX2-5, GATA-4, TBX5, NOTCH1.

The severity of illness and the way the body responds to treatments are also manifestations of genetic variations. For example, a single-base mutation in the APOE (apolipoprotein E) gene is associated with a lower risk for Alzheimer's disease. A single-nucleotide variant (SNV) is a variation in a single nucleotide without any limitations of frequency and may arise in cells. A single-nucleotide variation may also be called a single-nucleotide alteration. An MNP (Multiple-nucleotide polymorphisms) module 254 may identify the substitution of consecutive nucleotides at a specific position in the genome. An InDels module 256 may identify an insertion or deletion of bases in the genome of an organism classified among small genetic variations. While usually measuring from 1 to 10,000 base pairs in length, a microindel is defined as an indel that results in a net change of 1 to 50 nucleotides. Indels can be contrasted with a SNP or point mutation. An indel inserts and deletes nucleotides from a sequence, while a point mutation is a form of substitution that replaces one of the nucleotides without changing the overall number in the DNA. Indels, being either insertions, or deletions, can be used as genetic markers in natural populations, especially in phylogenetic studies. Indel frequency tends to be markedly lower than that of single nucleotide polymorphisms (SNP), except near highly repetitive regions, including homopolymers and microsatellites. An MSI (microsatellite instability) module 258 may identify genetic hypermutability (predisposition to mutation) that results from impaired DNA mismatch repair (MMR). The presence of MSI represents phenotypic evidence that MMR is not functioning normally. MMR corrects errors that spontaneously occur during DNA replication, such as single base mismatches or short insertions and deletions. The proteins involved in MMR correct polymerase errors by forming a complex that binds to the mismatched section of DNA, excises the error, and inserts the correct sequence in its place. Cells with abnormally functioning MMR are unable to correct errors that occur during DNA replication and consequently accumulate errors. This causes the creation of novel microsatellite fragments. Polymerase chain reaction-based assays can reveal these novel microsatellites and provide evidence for the presence of MSI. Microsatellites are repeated sequences of DNA. These sequences can be made of repeating units of one to six base pairs in length. Although the length of these microsatellites is highly variable from person to person and contributes to the individual DNA "fingerprint", each individual has microsatellites of a set length. The most common microsatellite in humans is a dinucleotide repeat of the nucleotides C and A, which occurs tens of thousands of times across the genome. Microsatellites are also known as simple sequence repeats (SSRs). Additionally, the alteration module 250 may include a tumor mutational burden module 260. A CNV (copy number variation) module 262 may identify deviations from the normal genome and any subsequent implications from analyzing genes, variants, alleles, or sequences of nucleotides. CNV are the phenomenon in which structural variations may occur in sections of nucleotides, or base pairs, that include repetitions, deletions, or inversions.

A Fusions module 264 may identify hybrid genes formed from two previously separate genes. It can occur as a result of translocation, interstitial deletion, or chromosomal inversion. Gene fusion plays an important role in tumorgenesis. Fusion genes which can contribute to tumor formation because fusion genes can produce much more active abnormal protein than non-fusion genes. Some genes that may cause heart disease in various forms and cause receptor mediated endocytosis, recycling, reculation abnormalities, cholesterol absorption or excretion, high blood pressure, atrial or ventricle defects, aortic defects, or offer other contributing factors for development of heart diseases includes: LDLR, APOB, ABCG5, ABCG8, ARH, PCSK9, ANGPTL3, SLC12A3, SLC12A1, KCNJ1, CLCNKB, NR3C2, SCNN1A, SCNN1B, SCNN1G, CYP11B2, CYP11B1, HSD11B2, NR3C2, SCNN1B, SCNN1G, WNK1, WNK4, KLHL3, CUL3, MYH7, TNNT2, TPM1, TNNI3, MYL2, MYBPC3, ACTC, MYL3, FBN1, NKX2-5, GATA-4, TBX5, NOTCH1.

Often, fusion genes are oncogenes that cause cancer; these include BCR-ABL, TEL-AML1 (ALL with t(12; 21)), AML1-ETO (M2 AML with t(8; 21)), and TMPRSS2-ERG with an interstitial deletion on chromosome 21, often occurring in prostate cancer. In the case of TMPRSS2-ERG, by disrupting androgen receptor (AR) signaling and inhibiting AR expression by oncogenic ETS transcription factor, the fusion product regulates prostate cancer. Most fusion genes are found from hematological cancers, sarcomas, and prostate cancer. BCAM-AKT2 is a fusion gene that is specific and unique to high-grade serous ovarian cancer. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. The latter is common in lymphomas, where oncogenes are juxtaposed to the promoters of the immunoglobulin genes. Oncogenic fusion transcripts may also be caused by trans-splicing or read-through events. Since chromosomal translocations play such a significant role in neoplasia, a specialized database of chromosomal aberrations and gene fusions in cancer has been created. This database is called Mitelman Database of Chromosome Aberrations and Gene Fusions in Cancer.

In some embodiments, an IHC (Immunohistochemistry) module 266 may identify antigens (proteins) in cells of a tissue section by exploiting the principle of antibodies binding specifically to antigens in biological tissues. IHC staining is widely used in the diagnosis of abnormal cells. Specific molecular markers are characteristic of particular cellular events such as proliferation or cell death (apoptosis). IHC is also widely used in basic research to understand the distribution and localization of biomarkers and differentially expressed proteins in different parts of a biological tissue. Visualising an antibody-antigen interaction can be accomplished in a number of ways. In the most common instance, an antibody is conjugated to an enzyme, such as peroxidase, that can catalyse a color-producing reaction in immunoperoxidase staining. Alternatively, the antibody can also be tagged to a fluorophore, such as fluorescein or rhodamine in immunofluorescence. Approximations from RNA expression data, H&E slide imaging data, or other data may be generated. For example, in some embodiments, the predictions may include PD-L1 prediction from H&E and/or RNA.

A Therapies module 268 may identify differences in cancer cells (or other cells near them) that help them grow and thrive and drugs that "target" these differences. Treatment with these drugs is called targeted therapy. For example, many targeted drugs go after the cells' inner 'programming' that makes them different from normal, healthy cells, while leaving most healthy cells alone. Targeted drugs may block or turn off chemical signals that tell the cancer cell to grow and divide; change proteins within the cancer cells so the cells die; stop making new blood vessels to feed the cancer cells; trigger your immune system to kill the cancer cells; or carry toxins to the cancer cells to kill them, but not normal cells. Some targeted drugs are more "targeted" than others. Some might target only a single change in cancer cells, while others can affect several different changes. Others boost the way your body fights the cancer cells. This can affect where these drugs work and what side effects they cause.

In some embodiments, matching targeted therapies may include identifying the therapy targets in the patients and satisfying any other inclusion or exclusion criteria. A VUS (variant of unknown significance) module 270 may identify variants which are called but cannot be classified as pathogenic or benign at the time of calling. VUS may be catalogued from publications regarding a VUS to identify if they may be classified as benign or pathogenic. A Trial module 272 may identify and test hypotheses for treating cancers having specific characteristics by matching features of a patient to clinical trials. These trials have inclusion and exclusion criteria that must be matched to enroll which may be ingested and structured from publications, trial reports, or other documentation.

An Amplifications module 274 may identify genes which increase in count disproportionately to other genes. Amplifications may cause a gene having the increased count to go dormant, become overactive, or operate in another unexpected fashion. Amplifications may be detected at a gene level, variant level, RNA transcript or expression level, or even a protein level. Detections may be performed across all the different detection mechanisms or levels and validated against one another.

An Isoforms module 276 may identify alternative splicing (AS), the biological process in which more than one mRNA (isoforms) is generated from the transcript of a same gene through different combinations of exons and introns. It is estimated by large-scale genomics studies that 30-60% of mammalian genes are alternatively spliced. The possible patterns of alternative splicing for a gene can be very complicated and the complexity increases rapidly as the number of introns in a gene increases. In silico alternative splicing prediction may find large insertions or deletions within a set of mRNA sharing a large portion of aligned sequences by identifying genomic loci through searches of mRNA sequences against genomic sequences, extracting sequences for genomic loci and extending the sequences at both ends up to 20 kb, searching the genomic sequences (repeat sequences have been masked), extracting splicing pairs (two boundaries of alignment gap with GT-AG consensus or with more than two expressed sequence tags aligned at both ends of the gap), assembling splicing pairs according to their coordinates, determining gene boundaries (splicing pair predictions are generated to this point), generating predicted gene structures by aligning mRNA sequences to genomic templates, and comparing splicing pair predictions and gene structure predictions to find alternative spliced isoforms.

A Pathways module may identify defects in DNA repair pathways which enable cancer cells to accumulate genomic alterations that contribute to their aggressive phenotype. DNA repair pathways are generally thought of as mutually exclusive mechanistic units handling different types of lesions in distinct cell cycle phases. Recent preclinical studies, however, provide strong evidence that multifunctional DNA repair hubs, which are involved in multiple conventional DNA repair pathways, are frequently altered in cancer. Identifying pathways which may be affected may lead to important patient treatment considerations. A Raw Counts module 278 may identify a count of the variants that are detected from the sequencing data. For DNA, this may be the number of reads from sequencing which correspond to a particular variant in a gene. For RNA, this may be the gene expression counts or the transcriptome counts from sequencing.

Disease state classification 280 may evaluate features from feature collection 205, alterations from alteration module 250, and other classifications from within itself from one or more classification modules 282*a-n*. Disease state classification 280 may provide classifications to stored classifications 230 for storage. An exemplary classification module may include a classification of a CNV as "Reportable" may mean that the CNV has been identified in one or more reference databases as influencing the disease state characterization, disease state, or pharmacogenomics, "Not Reportable" may mean that the CNV has not been identified as such, and "Conflicting Evidence" may mean that the CNV has both evidence suggesting "Reportable" and "Not Reportable." Furthermore, a classification of therapeutic relevance is similarly ascertained from any reference datasets mention of a therapy which may be impacted by the detection (or non-detection) of the CNV. Other classifications may include applications of machine learning algorithms, neural networks, regression techniques, graphing techniques, inductive reasoning approaches, or other artificial intelligence evaluations within modules 282_a-n_. A classifier for clinical trials may include evaluation of variants identified from the alteration module 250 which have been identified as significant or reportable, evaluation of all clinical trials available to identify inclusion and exclusion criteria, mapping the patient's variants and other information to the inclusion and exclusion criteria, and classifying clinical trials as applicable to the patient or as not applicable to the patient. Similar classifications may be performed for therapies, loss-of-function, gain-of-function, diagnosis, microsatellite instability, indels, SNP, MNP, fusions, and other alterations which may be classified based upon the results of the alteration modules 252_a-n_.

Each of the feature collection 205, alteration module 250, disease state 280 and feature store 120 may be communicatively coupled to data bus 290 to transfer data between each module for processing and/or storage. In another embodiment, each of the feature collection 205, alteration module 250, disease state 280 and feature store 120 may be communicatively coupled to each other for independent communication without sharing data bus 290.

Figure 3:
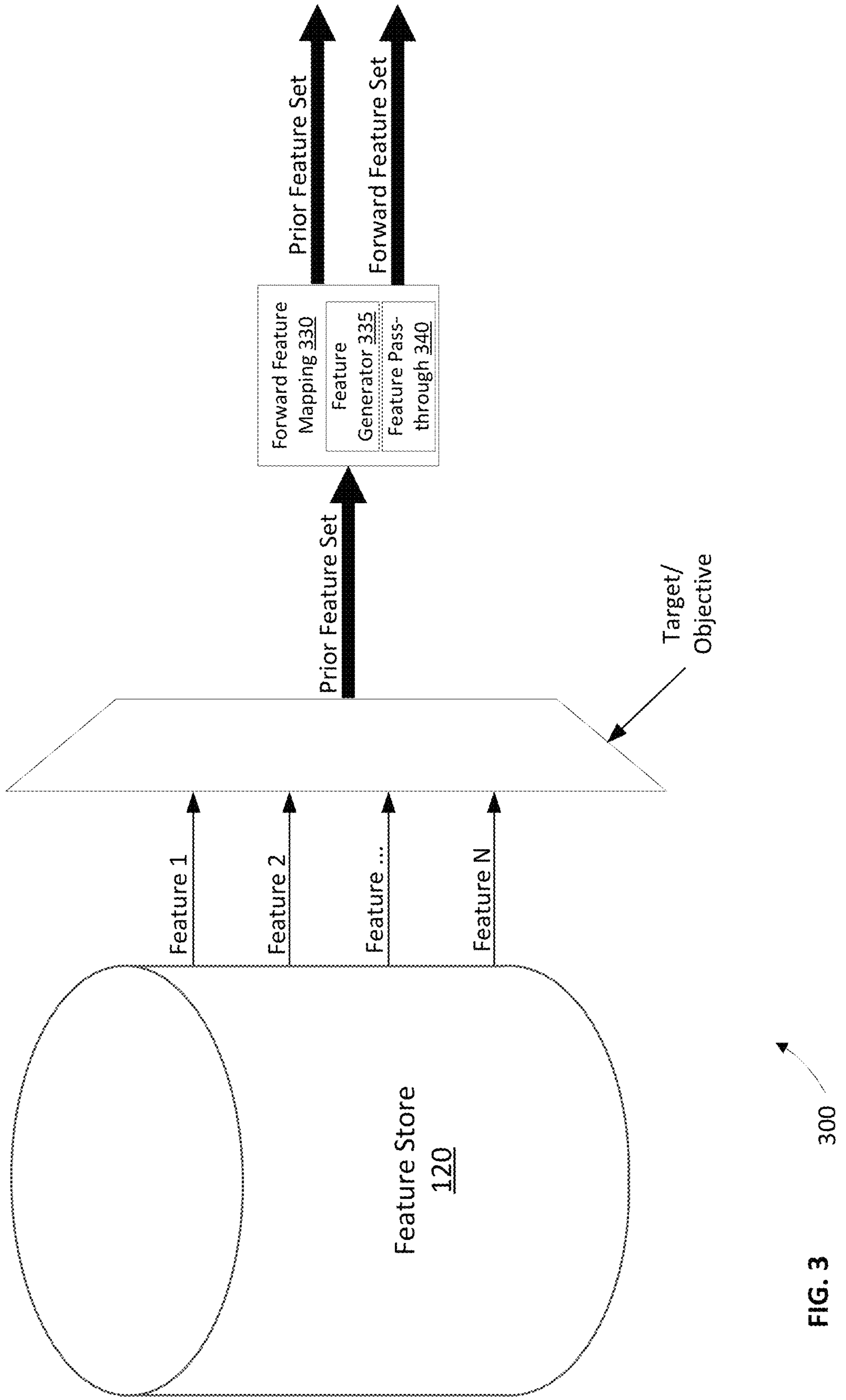
FIG. 3 is a schematic illustration of an example of a system for selecting a feature set for generating prior features and forward features based on a target/objective pair, in accordance with some embodiments of the present disclosure.
Figure 4:
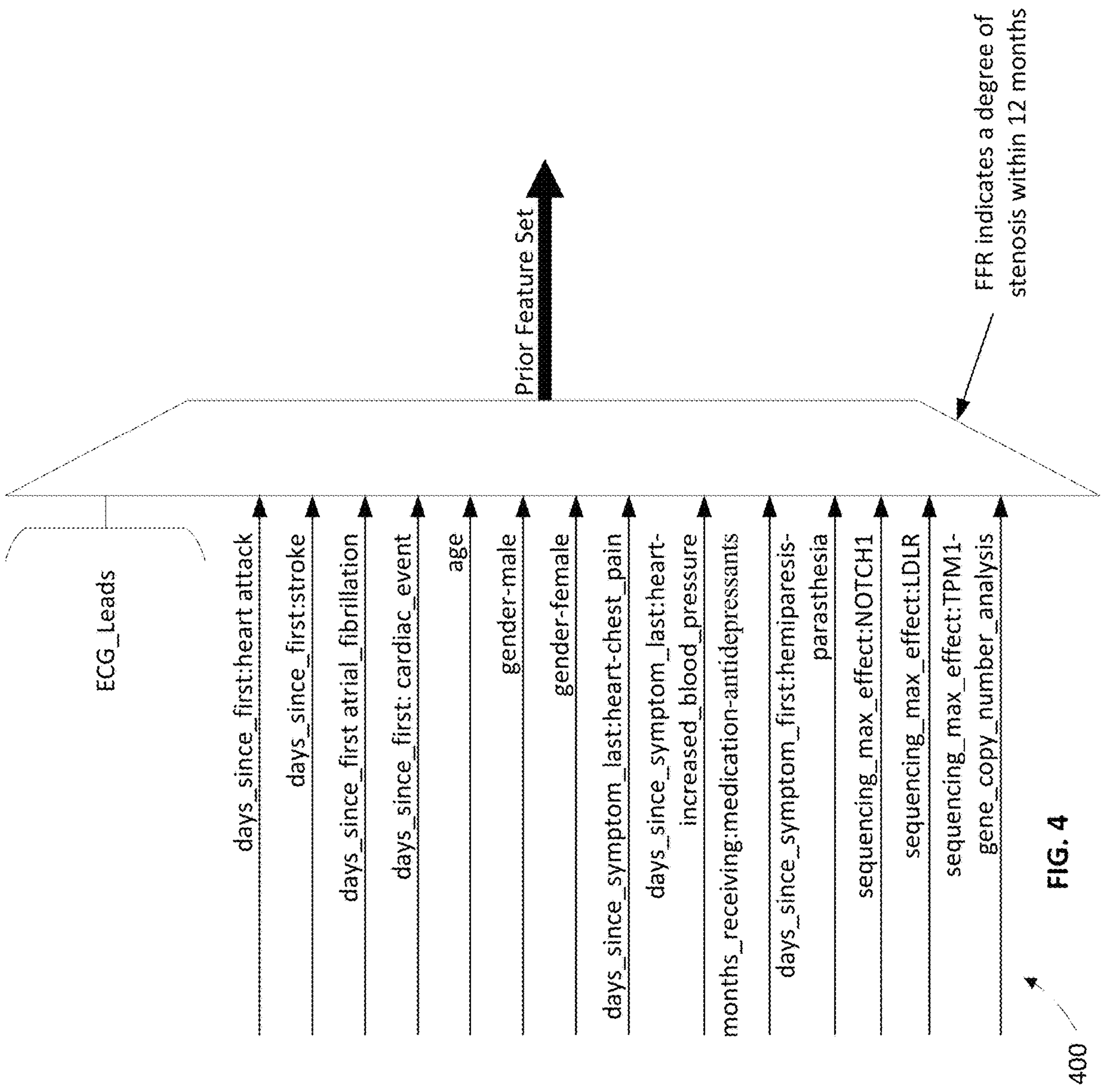
FIG. 4 is a schematic illustration of an example of a system for selecting a feature set for generating prior features based on predicting the likelihood that a patient's fractional flow reserve indicates a degree of stenosis within a defined period of time after an electrocardiogram, in accordance with some embodiments of the present disclosure.
Figure 5:
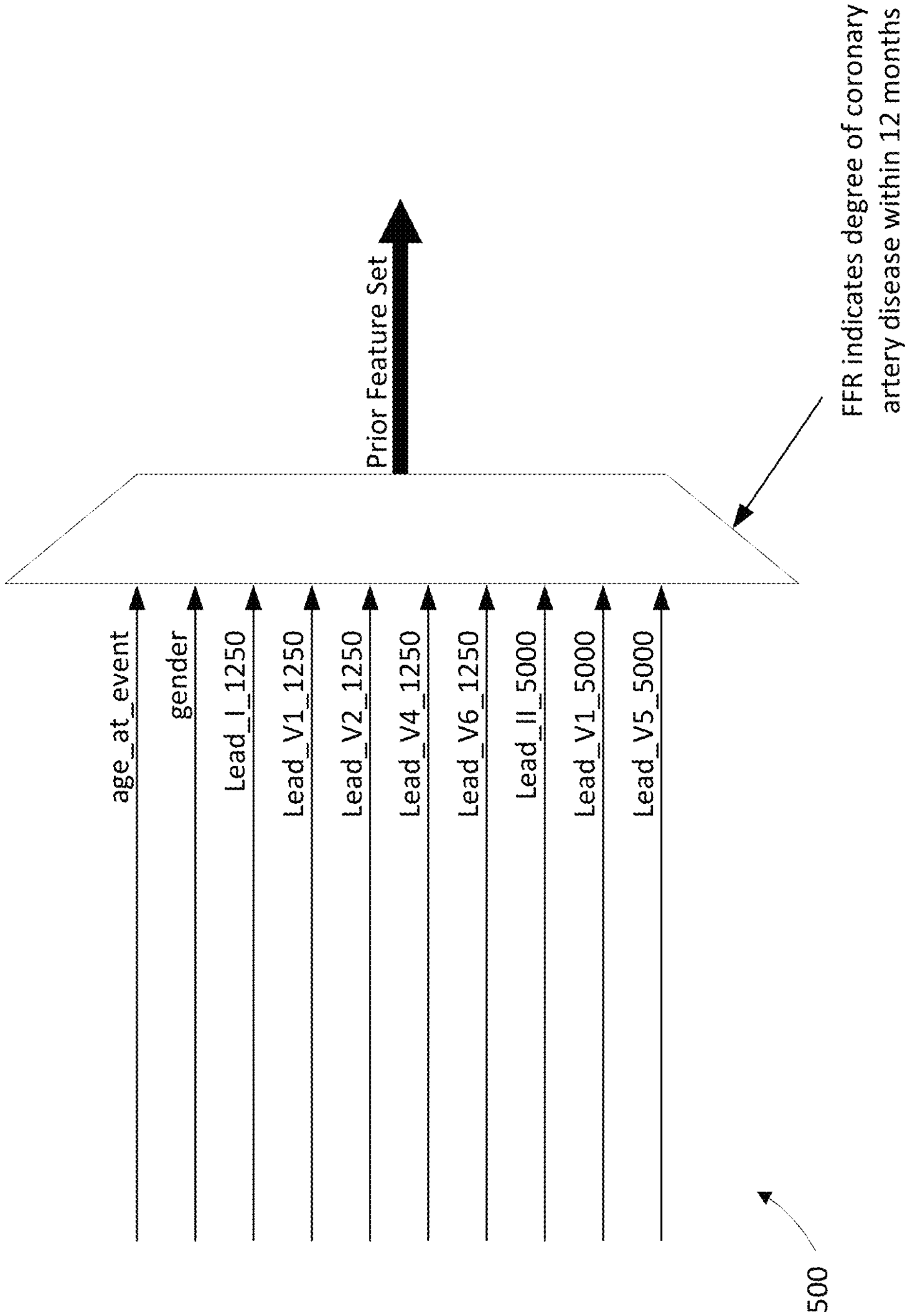
FIG. 5 is a schematic illustration of a system for selecting a feature set for generating prior features based from predicting the likelihood that a patient's fractional flow reserve indicates a degree of coronary artery disease within a defined period of time after an electrocardiogram, in accordance with some embodiments of the present disclosure.

FIGS. 3-5 illustrate the generation of feature sets from the feature store on a target/objective basis. FIG. 3 illustrates a system 300 for retrieving a first subset 1-N of features from the feature store 120. Different targets and objective modules may perform optimally on different feature sets. Feature selector and Prior feature set generator may select features 1-N based on the provided target and objective to produce an optimized, reduced feature set from which a patient-by-patient prior feature set may be generated. A prior feature set may be a collection of all features that occurred in a patient history before a specific date or may be an optimal collection of the best representative set of features satisfying the input requirements of a specific model, such as a model which has the best performance given the available features. For example, a patient with only DNA features may have a likelihood of disease state occurrence predicted from a model trained only on DNA features, whereas a patient with both DNA and clinical features may have a likelihood of disease state occurrence predicted from a model trained on both DNA and clinical features. In another example, a patient having sparsely populated features of numerous models, such as RNA, DNA, and clinical features, may evaluate expected performance from one or more combinations of the RNA, DNA, and clinical features alone and in combination to identify the best model and the set of features generated may be reduced to those that fit the optimal model. Other features, such as the specific date, may be selected from the current date at running of the model or any date in the past. In an exemplary likelihood that a patient will develop a disease state within a defined period of time prediction model, the specific date may be an anchor point corresponding to the time of genetic sequencing at a laboratory, such as when a genetic sequencing laboratory provides results of specimen sequencing. In some embodiments, the prior feature set may be automatically analyzed and the most appropriate model may be selected based on the analysis.

Predictions may be effective tools for data science analytics to measure the impact of treatments on the outcome of a patient's diagnosis, compare the outcomes of patients who took a medication against patients who did not, or whether a patient will develop a disease state in a specified time period. It may be advantageous to separate a patient's information into a collection of distinct prior feature sets and forward feature sets such that at every time point in the patient's history, predictions may be made and a more robust model generated that accurately predicts a patient's future satisfaction of a target/objective. A forward feature set may be advantageous when the predictive period for a target/objective combination begins to exceed a period of time that new information may be entered into the system 300. For example, a prediction that a patient may take a medication in the next 16-25 days has a limited window for new information from the date of prediction such that the prediction is unlikely to change based on information that becomes available within the next 16-25 days. However, a prediction that a patient's cancer will remain progression-free for the next 24 months may be greatly influenced by events that could happen in the next 24 months. Therefore, an exemplary system 300 may generate a forward feature set which looks to events that may occur during the prediction period at feature generator 335. In one embodiment, feature pass-through 340 may pass the prior feature set though the forward feature mapping 330 to objective modules 140 without generating an accompanying forward feature set, for example, when the prediction is unlikely to be improved by inclusion of a forward feature set.

As discussed above, the FFR Measurement objective module 146 may receive an ECG feature set, a combined ECG and observational feature set, or a combined ECG feature set, observational feature set and/or a DNA and/or RNA feature set. The FFR Measurement objective module may receive lab results from patients having an FFR Measurement, corresponding ECG data, and generate a model for predicting FFR Measurement from ECG absent a lab test. Additional lab results may include troponin or other cardiac related tests.

Various features may be generated and/or derived for a patient. For example, in some embodiments, the features can be related to RNA TPM (transcripts per million) count features. The feature space may comprise expression levels of the RNA for some or all of the coding genes in the sample. The expression is assayed by counting the number of RNA molecules (transcripts) that are present on a per gene basis. To standardize these counts across different experimental and technical conditions, the counts per gene can be corrected by a normalization factor. This factor standardizes the expression data to represent the number of RNA molecules that would be associated with a single gene in a pool of one million molecules, creating a TPM count.

In some embodiments, an input feature in a TPM space is a normalized count with a lower bound of 0, where the value represents the abundance of the transcript. Transcripts over the whole exome (nearly 19K genes) can be considered. For example, in some embodiments, the genes comprise LDLR, APOB, ABCG5, ABCG8, ARH, PCSK9, ANGPTL3, SLC12A3, SLC12A1, KCNJ1, CLCNKB, NR3C2, SCNN1A, SCNN1B, SCNN1G, CYP11B2, CYP11B1, HSD11B2, NR3C2, SCNN1B, SCNN1G, WNK1, WNK4, KLHL3, CUL3, MYH7, TNNT2, TPM1, TNNI3, MYL2, MYBPC3, ACTC, MYL3, FBN1, NKX2-5, GATA-4, TBX5, NOTCH1.

In some embodiments, the features generated for a patient may include RNA pathway features.

Previous experimental research has identified collections of functionally related genes, which are stored and collected in the MSigDB Molecular Signatures Database. RNA pathway features can be generated by performing single sample gene set enrichment analysis (ssGSEA) using the collections of gene sets and individual sample gene expression rankings. ssGSEA acts by ranking the RNA expression within a sample and then assigning a score to the gene set that is a function of that rank within the sample for the genes in the set. In practice, this functions to give high pathway scores to gene sets where all the genes in the set are highly expressed in the sample, and vice versa for lowly expressed genes. In practice, pathway scores serve to reduce some of the noise in the RNA expression feature space.

In an example, an input feature in RNA Pathway space is a numerical value between −1 and 1 indicating the coincident expression, either up-regulated or down-regulated, of all of the genes in the pathway grouping.

Referring back to FIG. 1, a model 146*b* may be generated for each of the potential feature sets or targets 146*a*. FIG. 4 illustrates an exemplary prior feature set 400 which may be generated for a target/objective combination for predicting FFR where the inputs narrowed to the prior features based on the target/objective of "degree of stenosis within a period of time" such as 12 months or 24 months. A sufficiently trained model may identify a combination of features including cardiac events such as atrial fibrillation, hemodynamic alteration, FFR abnormalities, stenosis, coronary artery disease, arrhythmia, irregular heartbeat, etc., date since diagnosis, gender, symptoms, and sequencing information as the most relevant features to predicting cardiac events of a patient. In some instances, a patient may be more likely to have a repeat cardiac event if there is a prior cardiac event on record, a patient is taking certain medications such as nonsteroidal anti-inflammatory drugs (NSAIDs), antidepressants, vitamin E, statins, hormone replacement therapy (HRT), and testosterone replacement therapy, the age of the patient may also play a role as adults may be more likely to experience a cardiac event than children, a male patient who smokes may be more likely to experience a cardiac event, a female patient post menopause may also be more likely to experience a cardiac event, symptoms implicating the heart from either discomfort such as chest pain, paresthesia or tingling in the patient's extremities, or a measurable increase in blood pressure may also increase the patient's likelihood for a cardiac event, and RNA/DNA sequencing results indicating a presence of a LDLR, APOB, ABCG5, ABCG8, ARH, PCSK9, ANGPTL3, SLC12A3, SLC12A1, KCNJ1, CLCNKB, NR3C2, SCNN1A, SCNN1B, SCNN1G, CYP11B2, CYP11B1, HSD11B2, NR3C2, SCNN1B, SCNN1G, WNK1, WNK4, KLHL3, CUL3, MYH7, TNNT2, TPM1, TNNI3, MYL2, MYBPC3, ACTC, MYL3, FBN1, NKX2-5, GATA-4, TBX5, NOTCH1 variation or copy number change may increase a patient's likelihood for experiencing a cardiac event. Therefore, a predictive model may select a subset of features from the feature store 120 including ECG leads recorded from an ECG, each of these features, and more, as identified by the optimal model given a patient's (or collection of patients') feature set(s).

FIG. 5 illustrates a prior feature selection set 500 for a target/objective pair FFR indicates degree of coronary artery disease within 12 months using a combined ECG, observational, and DNA sequencing feature set. In some embodiments, features of an observational model may be limited to features which may be observed from patient results from tests, progress notes, but not medications, procedures, therapies, or other proactive actions taken by a physician in treating the patient. General features in the observational feature set may include a patient's age at event for each event which may exist in the patient's record, patient's gender, and/or laboratory results such as for troponin or other cardiac testing. Preprocessing steps may be performed on the ages available to reduce the dimensionality of the input features. For example, instead of having 100+ points for ages of patients (1-100), the patient's age may be fitted into a group such as a range including 00 to 09, 10 to 19, 100 to 109, 110 to 119, 20 to 29, 30 to 39, 40 to 49, 50 to 59, 60 to 69, 70 to 79, 80 to 89, 90 to 99, or Unknown for each event in the patient's record. While a bin of ten years is exemplified, other bin sizes may be used. The reduction accomplished through binning features allows for a more robust analysis of the bins rather than the granular age. The patient's gender or race may be normalized so that different sources having different ethnicity options are binned into similar ethnicities. For example, a race of Caucasian, Scandinavian, or Irish, may be binned with white, a dataset including Japanese, Korean, Phillipean distinctions may be binned into Asian, a dataset with Hawaii, Guam, Tonga, Samoa, or Fiji may be binned into Pacific Islander, or a dataset with Cuban, Mexican, Puerto Rican, or South or Central American may be binned into Hispanic or Latino. Features which may be entered into the record by occurrence may be translated and tracked by a number of days since the first or last occurrence. Days since the first or last occurrence features may include a diagnosis of cardiac event occurrence including atrial fibrillation, hemodynamic alteration, FFR abnormalities, stenosis, coronary artery disease, arrhythmia, irregular heartbeat, etc.

Even other days since first or last occurrence features may include medical events, prior medications, or comorbidity or recurrence events including emergency_room_admission, inpatient_stay, seen_in_hospital_outpatient_department, Abnormal_findings_on_diagnostic_imaging, Anemia, Dehydration, Essential_hypertension, Fatigue, Long_term_current_use_of_drug_therapy, Osteoporosis, Past_history_of_procedure, chronic_obstructive_lung_disease, type_2_diabetes_mellitus, type_2_diabetes_mellitus_without_complication, emergency_room_admission, inpatient_stay, seen_in_hospital_outpatient_department. DNA and RNA features which have been identified from a next generation sequencing (NGS) of a patient's specimen to identify variants include categorizations of RNA expression analysis from an RNA auto encoder, DNA related features (DNA variant calls) may include a calculation of the maximum effect a gene may have from sequencing results for the gene set forth in Table 1, fluorescence_in_situ_hybridization (fish), gene_mutation_analysis, gene_rearrangement_analysis, or immunohistochemistry_(ihc) results. A patient's prior feature set may be selected from each of the above features identified within the patient's structured medical records available in the feature store 120. Illustrated in FIG. 5 is an example of a combined ECG and Observational feature set having 1250 signal values per short lead (Leads I, V2, V3, V4, V6), as well as 5000 signal values per long lead (II, V1, and V5), gender, and age. Prior feature sets from the feature generator may be provided to the corresponding model for the target/objective pair identified and predictions generated for the patient.

Figure 6:
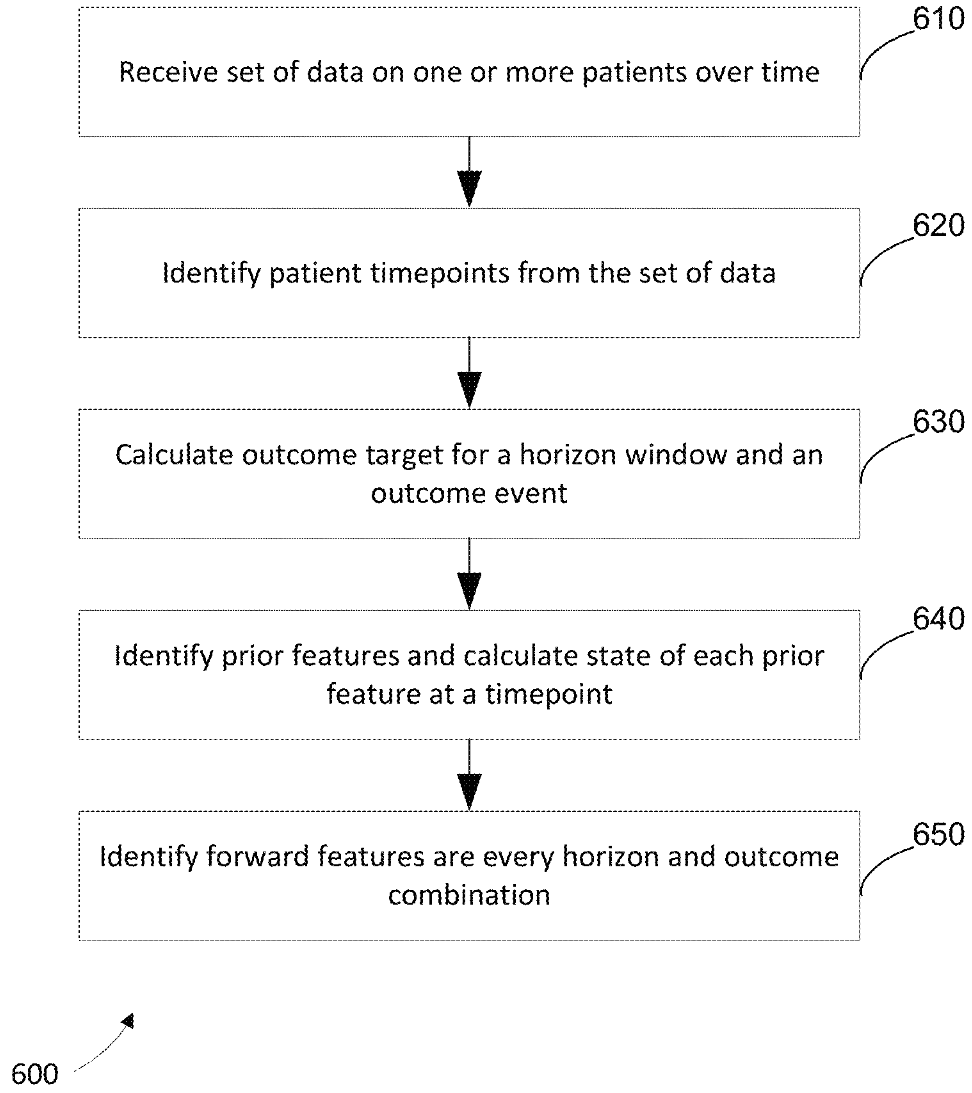
FIG. 6 is a flowchart illustrating a method for generating prior features and providing the prior features to a model for predicting the likelihood that a patient's fractional flow reserve indicates a degree of stenosis within a defined period of time after an electrocardiogram, in accordance with some embodiments of the present disclosure.

FIG. 6 is a flow chart of a method 600 for generating prior feature sets and forward feature sets in accordance with some embodiments. At step 610, the system may receive a set of data relating to one or more patients, wherein the data can be obtained over time. The received set of data may include features from the feature generation 130 as a refined feature set described above with respect to FIGS. 4 and 5. Patient records are received which may span from a single entry to decades of medical records. While these records indicate the status of the patient over time, they may be received in a single transmission or a batch of transmissions. Each patient may have hundreds of records in the system. An exemplary set of records for a patient may include physician note entries from a routine doctor's visit where the doctor prescribed an antibiotic after determining the patient has a bacterial infection, a scheduling request to see a specialist after the patient complained about headaches, scheduling request to take an ECG, an ECG report summarizing the technician's findings, scheduling request to take an MRI scan, an MRI report summarizing the radiologists findings of an unknown mass in the patient's lungs, a scheduling request to perform a biopsy of the mass, a pathologist's report of the cells present in the biopsy specimen, a prescription to begin a first line of therapy for lung cancer, an order for genetic sequencing of the biopsy specimen, any subsequent next-generation sequencing (NGS) report for the biopsy specimen, NGS sequencing requests for blood sample, saliva sample, urine sample, or other specimen of the patient, and any subsequent NGS report for the sequenced specimen.

At step 620, the system may identify patient timepoints based on the set of data. Identified timepoints may include all timepoints from patient diagnosis up to the last entry or patient's death. In some target/objective pairs, the only timepoint for identification is the most recent timepoint in which the patient received genetic sequencing results, such as, e.g., results from a next-generation sequencer for the genomic composition of the patient's specimen. An exemplary timepoint selection for FFR measurement prediction may include only the date that the ECG report for the patient was performed. In another embodiment, timepoint selection for a patient's likelihood to undergo a cardiac event (an event from which the heart condition worsens such as stenosis, stroke, atrial fibrillation, or other events known to those of ordinary skill in the art) may include timepoints from records: a report of a prior cardiac event, a prescription to begin a therapy for lowering blood pressure, the order for genetic sequencing of a specimen, and the subsequent next-generation sequencing report for the specimen.

At step 630, the system may calculate outcome targets for a horizon window and outcome event. Outcome events may be the objectives, and horizon windows may be the time periods such that an objective/target pair is calculated. An exemplary target/objective pair may be Atrial Fibrillation 142, Hemodynamic Alteration 144, FFR Measurement 146, and further additional models 148 which may include modules such as Medication or Treatment prediction, Adverse Response prediction, disease progression, disease recurrence, poor contact tracing classifiers, stenosis classifiers, coronary artery disease classifiers, arrhythmia classifiers, irregular heartbeat classifiers, or other predictive models (the objective) within 12 months (the target). The target/objective pair may also include the model from which the pair should be calculated. An exemplary model may be an ECG model, a combined ECG and observational model, or a combined ECG, observational and/or a DNA and/or RNA model. Other target/objective pairs, datasets, and models are introduced above with respect to objective modules 140. At step 640, the system may identify prior features and calculate the state of the prior features at each timepoint. For example, for a target/objective pair "FFR indicates degree of coronary artery disease within 12 months," as described above with respect to FIG. 5, the set of prior features may be calculated once, at the time of the patient undergoing an ECG. For a target objective pair "FFR Measurement indicates occurrence of cardiac event in next 12 months" the set of prior features may be calculated for each timepoint corresponding to the following records: a prior occurrence of a cardiac event, the prescription to begin a therapy for lowering blood pressure, the order for genetic sequencing of a specimen, and the subsequent next-generation sequencing report for the specimen.

At step 650 of FIG. 6, the system may identify forward features for every horizon and outcome combination where the horizon is of a sufficient duration that an event happening after the anchor point but before the termination of the timeline may have a noticeable effect on the reliability of the prediction. A forward feature set may be calculated for horizons spanning months or years. In some embodiments, forward feature sets are calculated for horizons spanning a certain number of days. Forward features comprise the same feature sets as prior features but involve a conversion of the features from a backwards looking focus to a forward looking focus. Exemplary forward features may include a computer-implemented determination of the following: "Will patient take a specific medication after date of anchor point and before date of endpoint?", "Will patient experience high blood pressure after date of anchor point and before date of endpoint", "Will patient experience a separate cardiac event after date of anchor point and before date of endpoint", or any other forward looking version of features in the prior feature set. Forward features may be predicted using another target/objective prediction, ensemble model first, and the predictions themselves added into the feature set to influence the final prediction. For example, a patient who is observing increased blood pressure may be predicted to experience headaches and a patient who experiences both increased blood pressure and headaches may be predicted to be more likely to have a stroke. A model which finds that a patient with an increase in blood pressure is likely to experience headaches within two weeks may provide additional features from which to inform the prediction of stroke. While the example is hypothetical, models may be trained to predict occurrence of each feature.

Figure 7:
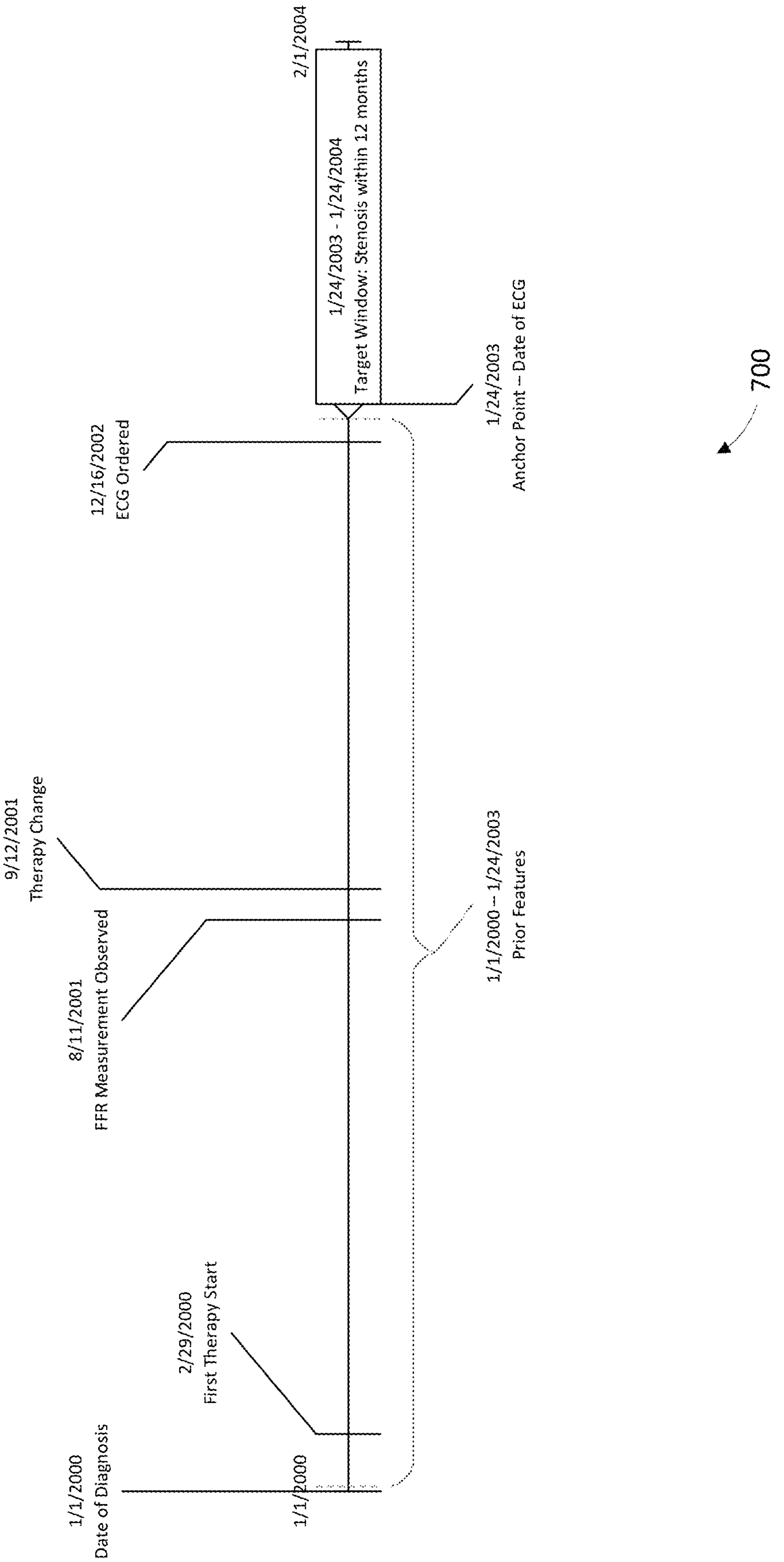
FIG. 7 is an illustration of an example of a patient timeline having events determining prior and forward features, in accordance with some embodiments of the present disclosure.

FIG. 7 illustrates an exemplary timeline of events 700 in a patient's medical record which may provide prior features for a prior feature set.

A patient's medical record may have a unique series of events, or interactions, as they face the challenges of rigoring through treatment for a disease. In patients who are diagnosed with a cardiac event, such as heart attack, some of these events may provide important features to prediction of a future occurrence of cardiac event for the patient. For an exemplary patient, the first event informing their prior feature set may be a progress note from the date of diagnosis (Jan. 1, 2000) containing the patient's information, diagnosis as congestive heart failure, systolic heart failure, left heart failure, diastolic heart failure, cardiomyopathy, or other heart failure, smoking record, record of smoking cessation counseling completion, a degree of severity, request for beta blockers, LVS function, and other features. The second event informing their prior feature set may be a prescription for medications of a therapy (Feb. 29, 2000) containing the patient's medications, dosages, and expected administration frequency. A third and fourth event may be a progress note from a physician which notes that an imaging scan of the heart (Aug. 11, 2001) shows that it has an FFR measurement increase since the therapy started and may prompt the physician to prescribe medications for another therapy triggering another progress note (Sep. 12, 2001)

containing the patient's new medications, dosages, and expected administration frequency.

The final events, or interactions, in the patient's medical record prior to triggering a prediction of the patient's site-specific prediction of FFR measurement to indicate a degree of stenosis may include a physician's order for an ECG (Dec. 16, 2002) and a subsequent ECG report (Jan. 24, 2003) comprising the results of that ECG. After a system, such as the system of FIGS. 1 and 4 processing FFR measurement to indicate a degree of stenosis predictions, detects presence of a stored ECG report, a model pipeline may trigger generation of the prediction. As another example, events, or interactions, which trigger generation of a prediction may include a physician's order for monitoring of the patient and a subsequent imaging report comprising the results of that imaging, including Mill, X-Ray, radiology image, or other imaging record such as a record to measure FFR.

In some embodiments, a model pipeline may include a plurality of models. When modeling with small sample sizes, random choice of specific patients for hold-out set evaluation can have a large impact on resulting performance. With different train-test patient assignments, a hold-out set ROC AUC score can be, in some implementations, of from 0.3 (considered to be worse than random) to 1.0 (considered to be a "perfect" model). In some embodiments, because of this large degree of variability, performance can be evaluated on a large number of different potential hold out sets, as opposed to relying on a single set of predefined train-test assignments.

In some embodiments, a modeling algorithm can include data preprocessing (log-transforming, one-hot encoding, imputing missing values, and in-line transformations such as z-scoring, dimensionality reduction methods, etc.), robust feature selection (a bootstrapped approach using lasso techniques, many different modifications of recursive feature elimination, Pearson correlation, correlated feature trimming, spectral biclustering, or other methods, hyper-parameter tuning (model selection from modifying the regularization strength in logistic regression, or number of estimators and maximum depth in a random forest, as examples), prediction generation (generating a probability between 0 and 1 for each patient at any given time horizon, from the tuned model), and feature importance evaluation (where features are identified which are driving, or correlated with the prediction). It should be appreciated, however, that any variations of the modeling algorithm are possible.

In some embodiments of the present disclosure, the entire modeling algorithm can be executed more than 100 times, each time with a different assignment of cross-validation folds and hold out set. This process results in over 100 out-of-fold cross validated scores on the training set and over 100 of hold-out (or test set) scores to allow for more robust evaluation of the model, given the chosen pipeline parameters, since it generates a distribution of performance metrics, as opposed to relying on single point estimates (which can have a large degree of variance). This approach improves both model development and understanding of model generalizability. For the model development, this allows us to more rigorously compare the potential benefit of change to the pipeline (e.g. a new feature selection method, modeling framework, etc.), by comparing the two distributions of model performance scores, instead of comparing two held-out score point estimates. In terms of model generalizability, the held-out score distribution gives a much better understanding of how the model can be expected to perform on completely unseen data.

Furthermore, the large number of sets of predictions can also allow making some estimate of confidence about each patient's predicted probability of cardiac events, since the pipeline will generate the large number (e.g., at least 100, or at least 200, or at least 300, or at least 400, or at least 500, or at least 1000) of different predictions for each patient, instead of only one single prediction. In addition, the repeated, multiple feature importance evaluations provide a more robust feature importance analysis, because such approach allows selecting most robust features based not only on one specific training set, but in a certain percentage of the large number of different training sets. A threshold can be used to determine which features are identified as robust.

Figure 8:
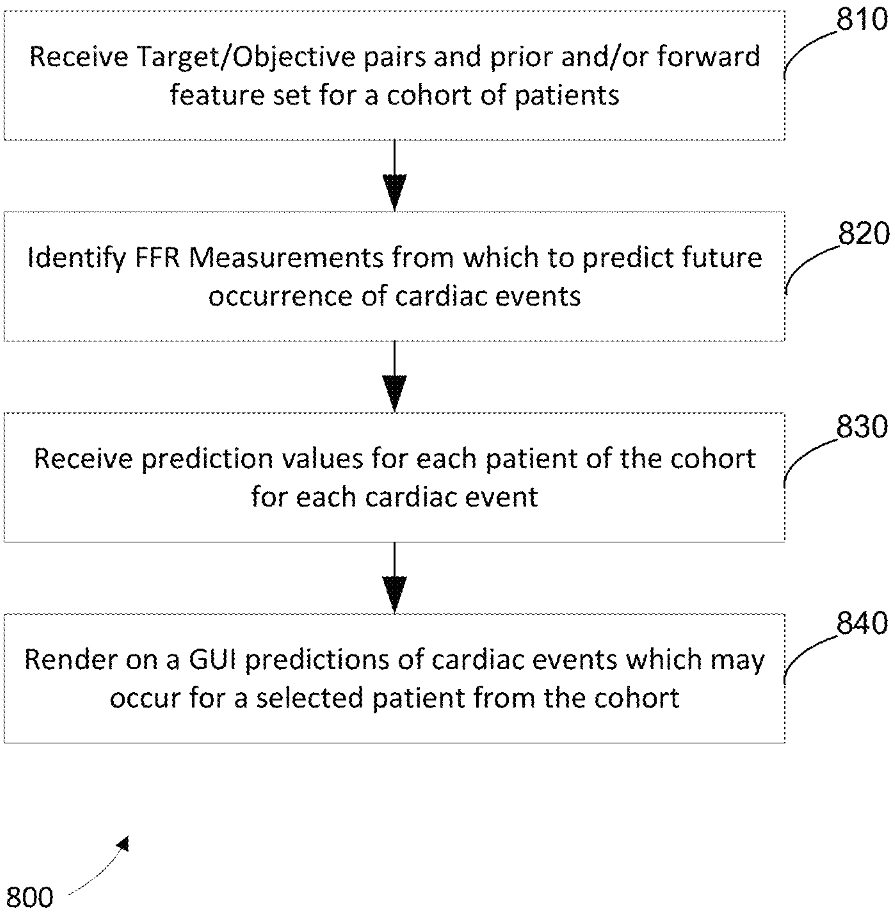
FIG. 8 is a flowchart illustrating a method for performing analytics in conjunction with application of a model for predicting hemodynamic alteration in a patient, in accordance with some embodiments of the present disclosure.

FIG. 8 illustrates an exemplary flowchart of a process 800 for applying a model for predicting site-specific cardiac events for a patient, in accordance with some embodiments of the present disclosure. The process 800 can be formed, for example, by the system 100 (FIG. 1) or by another suitable system.

At step 810, the system may receive target/objective pairs and prior feature set for a cohort of patients. The system may also receive a request to process one or more target/objective pairs from one or more prior and forward feature sets. Each target/objective pair may be matched with a specific combination of prior and/or forward feature sets based upon the requirements of a corresponding machine-learning model. At step 820, the system may identify FFR Measurements from which to predict future occurrence of cardiac events. In an embodiment, each of the target/objective pairs may reference a specific cardiac event which may be passed through to model selection directly. In other embodiments, a target/objective pair may not specify a specific cardiac event—e.g., the target/objective pair may define a request to predict whether any cardiac event may occur within 12 months. The system may then select a model trained for prediction of a certain cardiac event within the available models, and it can pass the matched target/objective pair and combination of prior and/or forward features to the model. At step 830, the system may receive prediction values for each patient of the cohort for each cardiac event. The predictions may be stored in a prediction store such as, e.g., the prediction store 150 or the predictions may be passed to webforms for displaying prediction results for the patient on a graphical user interface of a computing device of a user. The user can be, e.g., a patient's physician, cardiologist, or another medical professional. At step 840, the system may render, on the graphical user interface of the computing device, in a graphical form, predictions of FFR Measurement and likelihood of subsequent cardiac events for a patient of the cohort. The predictions of cardiac events can be, e.g., in the format of a likelihood of each cardiac event within a certain time period from the current time based on a result of ECG and prediction of FFR Measurement. The predictions can be displayed on the user interface in association with a computer-implemented representation of the likelihood of each cardiac event, or in other suitable format.

Figure 9A:
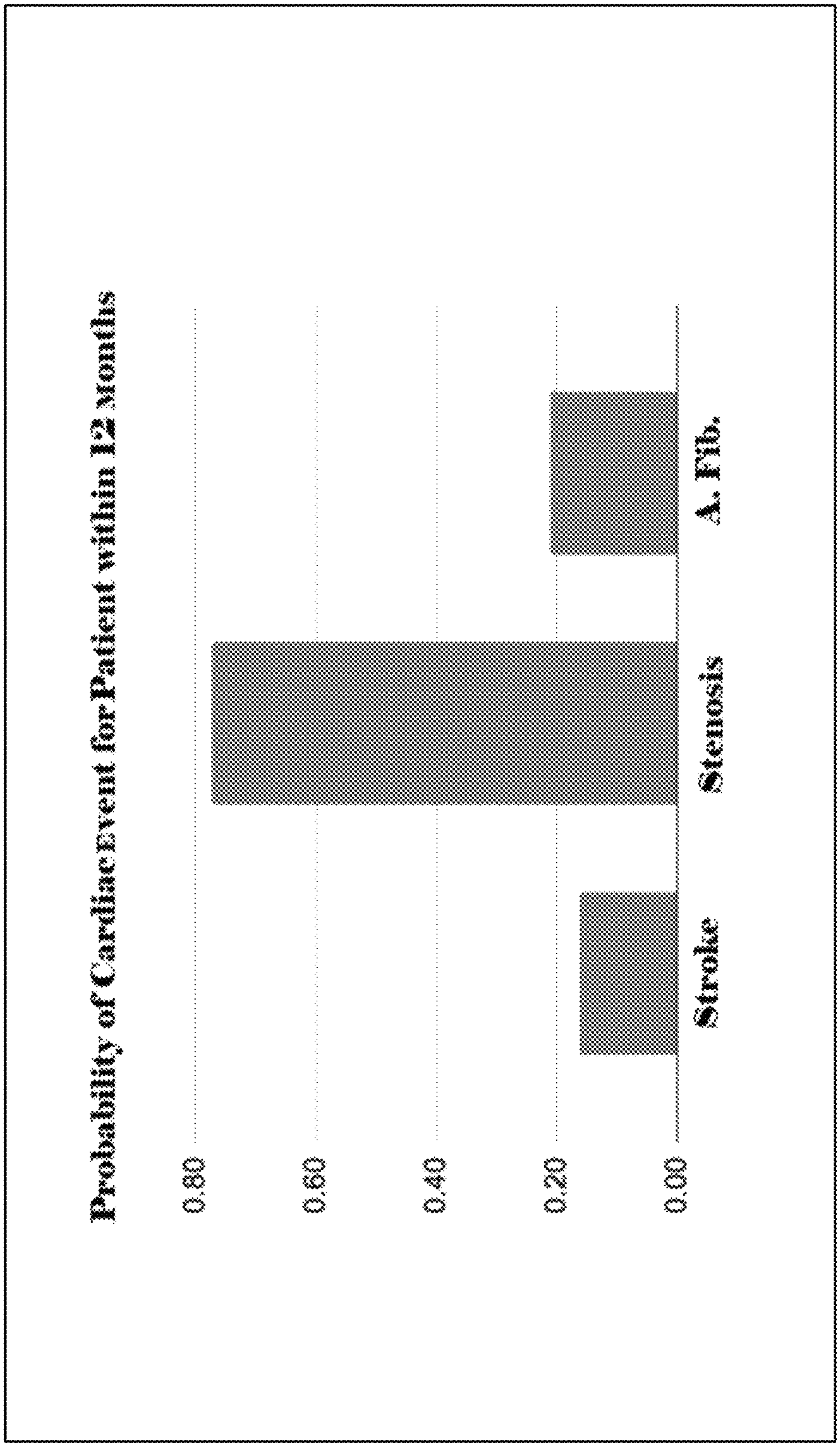
FIG. 9A illustrates an example of elements of a webform for viewing predictions of fractional flow reserve measurement in a patient, in accordance with some embodiments of the present disclosure.
Figure 9B:
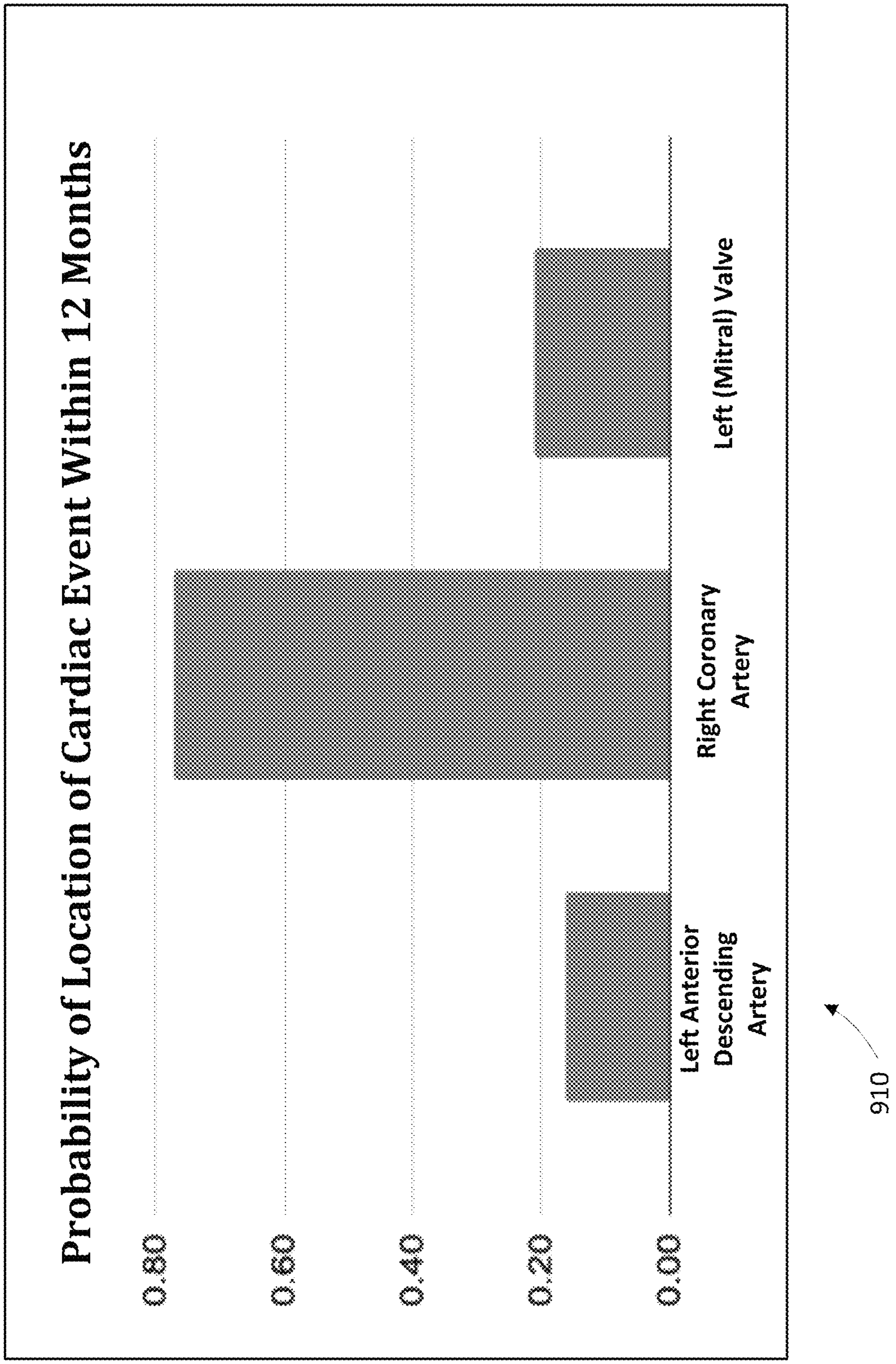
FIG. 9B illustrates a second example of elements of a webform for viewing predictions of fractional flow reserve measurement in a patient, in accordance with some embodiments of the present disclosure.
Figure 9C:
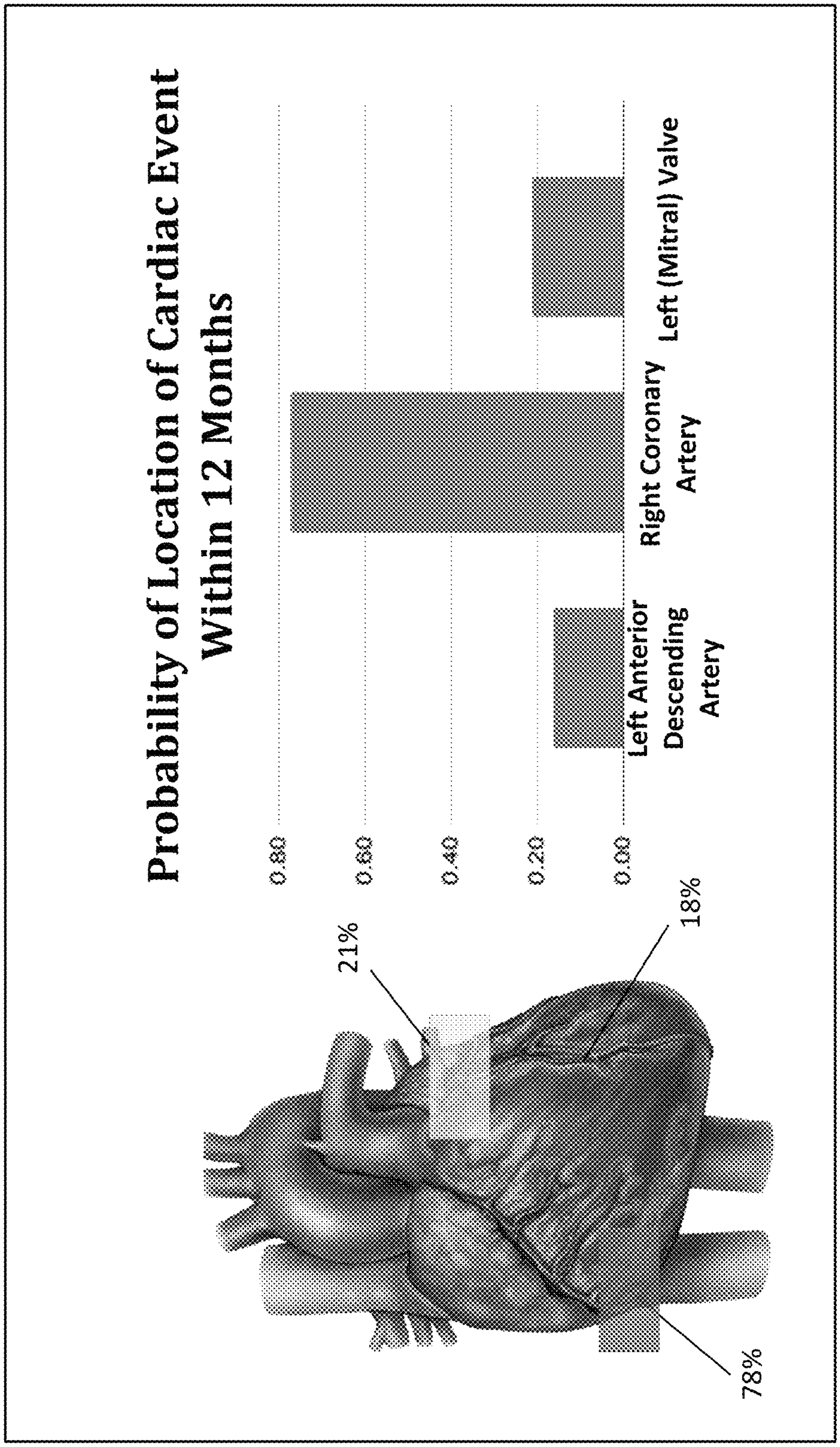
FIG. 9C illustrates a third example of elements of a webform for viewing predictions of fractional flow reserve measurement in a patient, in accordance with some embodiments of the present disclosure.

In some embodiments, the graph, images, and/or other information may be generated in a corresponding webform for viewing the results of event-specific cardiac event predictions. Cardiac event predictions associated with the target/objective pair may be listed and/or analytics may be viewed. Analytics may include the prediction percentages, survival curves of the cohort, or features which were driving factors in the prediction results generated. Examples of a webform for displaying the graph are shown in FIGS. 9A-C, discussed below.

Applications of predictions may include providing precision medicine results for a patient. For example, a sample obtained from a patient may be subjected to genetic sequencing during a course of treatment for a heart failure diagnosis. Predictions may be generated based upon the patient's genetic sequencing results and ECG results, which provide insights on the patient's response to particular therapies. A physician may receive recommended considerations as a component of a reporting of the genetic sequencing as a precision medicine result for the patient. Results may include therapies which are expected to perform well for a patient having characteristics similar to the reported patient, clinical trials which may accept the patient, or results of the sequencing which may influence the physician's decisions. In one example, a patient may be prescribed a treatment which is considered aggressive for the treatment and prevention of future cardiac events. A prediction may be generated that the patient, based upon their particular genetics and clinical history, are unlikely to experience heart failure within the next 6 months. A physician may then decide to suggest a less aggressive treatment to the patient which may reduce the negative side effects related to a harsher, more aggressive treatment and may be cheaper.

In another example, a patient may be prescribed an introductory treatment which is not considered aggressive just to see how the patient responds. A prediction may be generated that the patient, based upon their particular genetics, clinical history, and most recent imaging reports are likely to experience coronary artery disease within the next 12 months. A physician may then decide to suggest a more aggressive treatment to reduce the chance that the patient may experience another cardiac event. Considerations made by the physician are not limited to treatments, as a physician may utilize predictions to schedule the frequency of monitoring for the patient, such as follow-up visits, additional scanning, screening, imaging, blood tests, or subsequent genetic sequencing. For example, a patient with a high prediction of aortic stenosis may benefit from accelerated screening to detect changes as they occur rather than months after they occur and the patient is experiencing noticeable side effects. In another example, a pharmaceutical company testing a new drug may select potential test groups both off of their current inclusion and exclusion criteria and the probability that the patient will experience a predicted outcome.

In another example, a pharmaceutical company may retroactively analyze the predicted outcome of patients in a clinical trial against how they responded to identify patient characteristics which may be included as inclusion or exclusion criteria in a future clinical trial. For example, patients which responded well to treatment and had a high prediction for successful response to treatment may have features, or status characteristics, in common which are absent from the patients which did not respond well to treatment.

FIGS. 9A-9C illustrate examples of webforms for viewing site-specific predictions of cardiac events in a single patient. The webforms can be displayed on a GUI of a user device (e.g., the GUI 165 of FIG. 1).

An exemplary webform may provide a patient portal to a user, such as, e.g., a physician, cardiologist, or patient, that may request predictions of future cardiac events based upon a target/objective scheme. For example, a user may request a prediction of aortic stenosis in the next 12 months or a prediction of any cardiac event in the next 6 months. The system, such as system 100 of FIG. 1, may either calculate a prediction on the fly or retrieve a precalculated prediction from the prediction store 150 and provide the webform with the prediction information for display to the user. In one embodiment, a user may request a prediction of any cardiac event in 12 months. The webform may receive the predictions and display them to the user through the user interface of the webform 900, as seen in FIG. 9A. In another embodiment, a user may request a prediction of a particular cardiac event such as a lesion or other obstruction at one or more locations within the heart within a particular time such as the next 12 months. The webform again may receive the predictions and display them to the user through the user interface of the webform 910, as seen in FIG. 9B, indicating a probability of the specific cardiac event at the different locations.

The cardiac event sites may be displayed in a number of different formats. As seen in FIG. 9C, a first format may include an image of a human body which regions having cardiac event predictions highlighted therein. Highlighting for regions with predictions may be color coded based upon the value of the prediction. For example, elements/organs/sites of the human body which do not have predictions may not be referenced in the image, such as the brain, blood vessels, or heart. A prediction falling below a threshold of 20% may receive a callout such as a line or other indicator linking the organ to the prediction threshold, such as blood vessels with a line a prediction value (e.g. 16%). A prediction falling between 20% and 50% may receive a callout linking the organ to the prediction threshold and a color coded shading over the region indicating the severity of the prediction, such as the left valve of the heart, or the whole heart with a line to the prediction value 41% and a green shading over the region where a heart would be in a human. A prediction falling between 50% and 75% may receive a callout linking the organ to the prediction threshold and a color-coded shading over the region indicating the severity of the prediction, for example a yellow shading over the region where the cardiac event would be in a human. A prediction exceeding 75% may receive a callout linking the organ to the prediction threshold and a color coded shading over the region indicating the severity of the prediction, such as blood vessels with a line to the prediction value 77% and a red shading over the region where major arteries would be in a human.

The above prediction ranges and combination of callout styles and color shading are provided for illustrative purposes and are not intended to limit the display to the user. Other combinations of prediction ranges, callout conventions, and/or coloring may be provided to the user without departing from the spirit of the disclosure. In addition to or as an alternative to the first format, a second format may include a histogram or bar chart which provides a side by side comparison of the predictions for differing cardiac events. For example, a patient may have event predictions for stroke, stenosi, and atrial fibrillation events. A histogram may display the predicted values of each side-by-side to provide the user with a visual comparison of the likelihood of cardiac events to each site. Other statistical, analytical, or graphical representations may be provided including charts, plots, and graphs such as prediction distribution Kernel Density Estimate (KDE) plots, violin plots, per patient time series line plots of predicted likelihood of experience cardiac events over time, etc.

Figure 10:
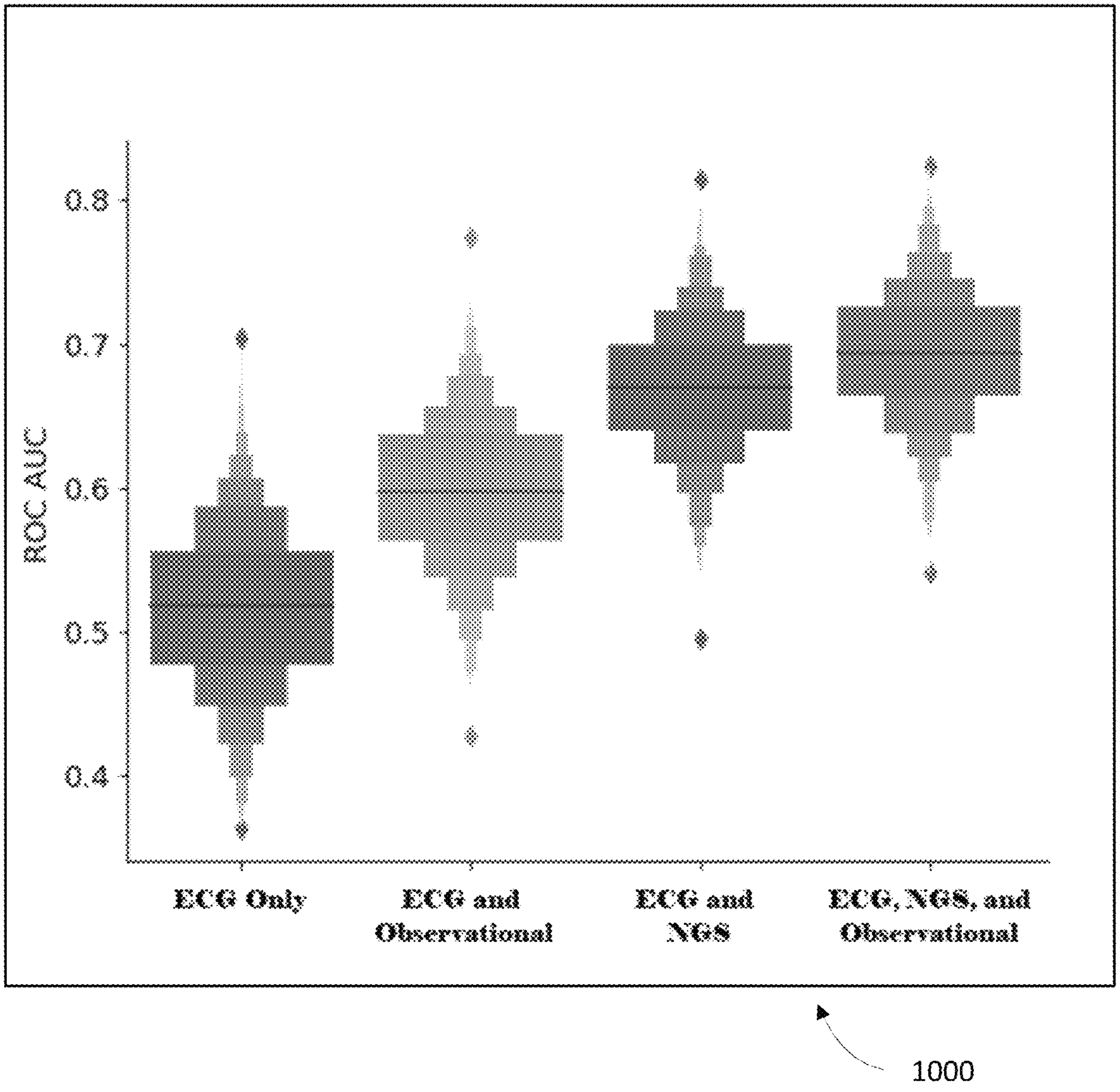
FIG. 10 illustrates an example of aggregate measures of performance across classification thresholds of input data sets according to an objective of likelihood that a patient's fractional flow reserve indicates a degree of stenosis within a defined period of time after an electrocardiogram, in accordance with some embodiments of the present disclosure.

FIG. 10 is an illustration 1000 of exemplary aggregate measures of performance across possible classification thresholds of input data sets according to an objective of predicting cardiac events in patients within 12 months.

As discussed above with respect to FIG. 1, there are a number of models which may be selected and for each model there are a number of tuning parameters which may be considered. For an objective of degree of stenosis based from FFR Measurement prediction, the collection of cardiac events at each time point may be used as the target of interest. The cardiac events which may be considered include atrial fibrillation, hemodynamic alteration, FFR abnormalities, stenosis, coronary artery disease, arrhythmia, irregular heartbeat, etc., with any other sites being grouped into a miscellaneous category. Other combinations of cardiac events may be considered as well. During preprocessing, it may be advantageous to impose an additional requirement that each target must have more than one unique value within every cross validation fold in order to ensure the sites at which predictions are generated are variable depending on the cardiac event predicted to occur.

Given a curated dataset with the five most common cardiac events in a cohort of all events, it may be advantageous to tune a multilabel random forest using 4 batches of 5 jobs, optimizing the average area under curve (AUC) across all target labels. In general, the models seem to prefer a large number of deep trees with heavy column sampling at each split, which could be used to improve future tuning jobs.

Given a known set of hyperparameters for each objective, it may be advantageous to consider the impacts of a selected feature set for each objective. For example, a feature set for ECG data only, may include a plurality of ECG records for each lead in an ECG. Leads may include a variable length, in one example, all leads may have a length of 1000, 1250, 5000, or any other number of stored voltages for the lead sampled at any period of time including 1000, 800, 500, 100 reads per second. In one example, the ECG may include resting 12-lead electrocardiograms (ECGs) such as 1250 signal values short leads (e.g., Leads I, V2, V3, V4, V6) or 5000 signal values per long, rhythm ECG lead (e.g., Leads II, V1, V5), and a predicted fractional flow reserve measurement between 0-1. In one example, Tensorflow via Keras may be utilized to build a neural network utilizing 1D convolutional blocks with a batch normalization later. Activation functions may be assigned as a restructure linear unit, and a batch size of 64 may be selected. Leads having 1250 signal values may be provided to a first branch and leads having 5000 signal values may be provided to a second branch. These two branches may then be provided to a fully connected convolutional layer which, in turn, may be connected to an output node with sigmoid function (or softmax function) for prediction. The sigmoid function may receive additional information such as the age or sex of the patient, or a predicted FFR Measurement in order to improve the prediction reliability. In one example, an ADAM optimizer may be selected with a binary crossentropy loss function to train the model.

ECG Inputs Only

An ECG may include resting 12-lead electrocardiograms (ECGs) such as 1250 signal values short leads (e.g., Leads I, V2, V3, V4, V6) or 5000 signal values per long, rhythm ECG lead (e.g., Leads II, V1, V5) having voltages associated with each lead over a period of time.

In some examples, for a cardiac event prediction model trained on ECG only, a resulting receiver operating characteristic (ROC) area under curve (AUC) may be approximately 0.52.

ECG & Observational Inputs Only

In addition to ECG features from an ECG, a model may include observational features.

A feature set for an observational model may be limited to features which may be observed from patient results from tests, progress notes, but not medications, procedures, therapies, or other proactive actions taken by a physician in treating the patient. General features in the observational feature set may include a patient's age at event for each event which may exist in the patient's record, patient's gender, and/or laboratory results such as for troponin or other cardiac testing. Preprocessing steps may be performed on the ages available to reduce the dimensionality of the input features. For example, instead of having 100+ points for ages of patients (1-100), the patient's age may be fitted into a group such as a range including 00 to 09, 10 to 19, 100 to 109, 110 to 119, 20 to 29, 30 to 39, 40 to 49, 50 to 59, 60 to 69, 70 to 79, 80 to 89, 90 to 99, or Unknown for each event in the patient's record. While a bin of ten years is exemplified, other bin sizes may be used. The reduction accomplished through binning features allows for a more robust analysis of the bins rather than the granular age. The patient's gender or race may be normalized so that different sources having different ethnicity options are binned into similar ethnicities. For example, a race of Caucasian, Scandinavian, or Irish, may be binned with white, a dataset including Japanese, Korean, Filipino distinctions may be binned into Asian, a dataset with Hawaii, Guam, Tonga, Samoa, or Fiji may be binned into Pacific Islander, or a dataset with Cuban, Mexican, Puerto Rican, or South or Central American may be binned into Hispanic or Latino. Features which may be entered into the record by occurrence may be translated and tracked by a number of days since the first or last occurrence. Days since the first or last occurrence features may include a diagnosis of cardiac event occurrence including atrial fibrillation, hemodynamic alteration, FFR abnormalities, stenosis, coronary artery disease, arrhythmia, irregular heartbeat, etc.

Even other days since first or last occurrence features may include medical events, prior medications, or comorbidity or recurrence events including emergency_room_admission, inpatient_stay, seen_in_hospital_outpatient_department, Abnormal_findings_on_diagnostic_imaging, Anemia, Dehydration, Essential_hypertension, Fatigue, Long_term_current_use_of_drug_therapy, Osteoporosis, Past_history_of_procedure, chronic_obstructive_lung_disease, type_2_diabetes_mellitus, type_2_diabetes_mellitus_without_complication, emergency_room_admission, inpatient_stay, seen_in_hospital_outpatient_department. DNA and RNA features which have been identified from a next generation sequencing (NGS) of a patient's specimen to identify variants include categorizations of RNA expression analysis from an RNA auto encoder, DNA related features (DNA variant calls) may include a calculation of the maximum effect a gene may have from sequencing results for the gene set forth in Table 1, fluorescence_in_situ_hybridization_(fish), gene_mutation_analysis, gene_rearrangement_analysis, or immunohistochemistry_(ihc) results. A patient's prior feature set may be selected from each of the above features identified within the patient's structured medical records available in the feature store 120. Illustrated in FIG. 5 is an example of a combined ECG and Observational feature set having 1250 signal values per short lead (Leads I, V2, V3, V4, V6), as well as 5000 signal values per long lead (II, V1, and V5), gender, and age. Prior feature sets from the feature generator may be provided to the corresponding model for the target/objective pair identified and predictions generated for the patient.

Observational features may be assigned weights manually when setting up the model for cardiac event location prediction, may be assigned weights automatically via an external weighting model, or assigned weights automatically via model itself through a process called stacking.

In some examples, for a cardiac event prediction model trained on ECG and Observational features, the resulting ROC AUC may be approximately 0.60 which is greater than that of processing ECG features only.

ECG & NGS Only

The resulting ROC AUC may be approximately 0.67 which is greater than that of processing ECG only and ECG and Observational features only.

NGS may include DNA, RNA, or DNA and RNA sequencing results.

DNA related features (DNA variant calls) may include a calculation of the maximum effect a gene may have from sequencing results for the gene and source set forth in Table 1. A max effect calculation may include identifying an integer in a range from 0 to 7, wherein a 0 represents no effect and a 7 represents the highest effect a gene may impact a patient's diagnosis of cardiac event. While the values 0-7 are used for illustrative purposes, other values may be used according to a desired resolution for measuring the effect. Values of differing degrees may be awarded when mitigating or aggravating factors are present. For example, a variant which has substantial documentation within the medical community for causing/effecting a cardiac event may be assigned a higher value than a variant which has nominal documentation within the medical community for causing/effecting a cardiac event. In one example, genetic variants are assigned a max effect value and a model may be trained on a variant by variant basis. A variant by variant model may be trained on variant max effects and a supervisory signal identifying patient cardiac events. In another example, genetic variants are assigned a max effect value, but a model may be trained on a gene by gene basis. Converting variant max effect into gene max effect may include a number of approaches such as taking the highest max effect or applying customized weights to each max effect based upon the number of reads associated with the variant from sequencing of the patient's specimen. In one example, where the highest max effect is assigned, variants for each gene are compared to identify the highest max effect relating to the gene, and the highest max effect is assigned to the gene. Where the max effects are provided a customized weighting schema, each variant may be assigned a weight to scale the max effect and those max effects are combined into a gene max effect. For example, a gene with four identified variants may scale each max effect by 0.25 and sum the combined, scaled max effects into a gene max effect, effectively averaging the max effects. In another aspect, a gene with four variants having raw reads of 25, 100, 250, and 75 may scale each max effect by 25/450, 100/450, 250/450, and 75/450 respectively. A gene with no called variants (variants identified in the patient's genome) for a particular gene is assigned a max effect of 0.

TABLE 1

| |
|---|
| ABCB1 |
| ACTA2 |
| ACTC1 |
| ALK-fluorescence_in_situ_hybridization_(fish) |
| ALK-immunohistochemistry_(ihc) |
| ALK-md_dictated |
| ALK |
| AMER1 |
| APC-gene_mutation_analysis |
| APC |
| APC |

TABLE 1-continued

| |
|---|
| APOB |
| APOB |
| AR |
| ARHGAP35 |
| ARID1A |
| ARID1B |
| ARID2 |
| ASXL1 |
| ATM-gene_mutation_analysis |
| ATM |
| ATM |
| ATP7B |
| ATR |
| ATRX |
| AXIN2 |
| BACH1 |
| BCL11B |
| BCLAF1 |
| BCOR |
| BCORL1 |
| BCR |
| BMPR1A |
| BRAF-gene_mutation_analysis |
| BRAF-md_dictated |
| BRAF |
| BRCA1 |
| BRCA1 |
| BRCA2 |
| BRCA2 |
| BRD4 |
| BRIP1 |
| CACNA1S |
| CARD11 |
| CASR |
| CD274-immunohistochemistry_(ihc) |
| CD274-md_dictated |
| CDH1 |
| CDH1 |
| CDK12 |
| CDKN2A-immunohistochemistry_(ihc) |
| CDKN2A |
| CDKN2A |
| CEBPA |
| CEBPA |
| CFTR |
| CHD2 |
| CHD4 |
| CHEK2 |
| CIC |
| COL3A1 |
| CREBBP |
| CTNNB1 |
| CUX1 |
| DICER1 |
| DOT1L |
| DPYD |
| DSC2 |
| DSG2 |
| DSP |
| DYNC2H1 |
| EGFR-gene_mutation_analysis |
| EGFR-immunohistochemistry_(ihc) |
| EGFR-md_dictated |
| EGFR |
| EGFR |
| EP300 |
| EPCAM |
| EPHA2 |
| EPHA7 |
| EPHB1 |
| ERBB2-fluorescence_in_situ_hybridization_(fish) |
| ERBB2-immunohistochemistry_(ihc) |
| ERBB2-md_dictated |
| ERBB2 |
| ERBB3 |
| ERBB4 |
| ESR1-immunohistochemistry_(ihc) |
| ESR1 |
| ETV6 |
| FANCA |

TABLE 1-continued

| |
|---|
| FANCA |
| FANCD2 |
| FANCI |
| FANCL |
| FANCM |
| FAT1 |
| FBN1 |
| FBXW7 |
| FGFR3 |
| FH |
| FLCN |
| FLG |
| FLT1 |
| FLT4 |
| GATA2 |
| GATA3 |
| GATA4 |
| GATA6 |
| GLA |
| GNAS |
| GRIN2A |
| GRM3 |
| HDAC4 |
| HGF |
| IDH1 |
| IKZF1 |
| IRS2 |
| JAK3 |
| KCNH2 |
| KCNQ1 |
| KDM5A |
| KDM5C |
| KDM6A |
| KDR |
| KEAP1 |
| KEL |
| KIF1B |
| KMT2A-fluorescence_in_situ_hybridization_(fish) |
| KMT2A |
| KMT2B |
| KMT2C |
| KMT2D |
| KRAS-gene_mutation_analysis |
| KRAS-md_dictated |
| KRAS |
| LDLR |
| LMNA |
| LRP1B |
| MAP3K1 |
| MED12 |
| MEN1 |
| MET-fluorescence_in_situ_hybridization_(fish) |
| MET |
| MKI67-immunohistochemistry_(ihc) |
| MKI67 |
| MLH1 |
| MSH2 |
| MSH3 |
| MSH6 |
| MSH6 |
| MTOR |
| MUTYH |
| MYBPC3 |
| MYCN |
| MYH11 |
| MYH11 |
| MYH7 |
| MYL2 |
| MYL3 |
| NBN |
| NCOR1 |
| NCOR2 |
| NF1 |
| NF2 |
| NOTCH1 |
| NOTCH2 |
| NOTCH3 |
| NRG1 |
| NSD1 |
| NTRK1 |

TABLE 1-continued

| |
|---|
| NTRK3 |
| NUP98 |
| OTC |
| PALB2 |
| PALLD |
| PBRM1 |
| PCSK9 |
| PDGFRA |
| PDGFRB |
| PGR-immunohistochemistry_(ihc) |
| PIK3C2B |
| PIK3CA |
| PIK3CG |
| PIK3R1 |
| PIK3R2 |
| PKP2 |
| PLCG2 |
| PML |
| PMS2 |
| POLD1 |
| POLD1 |
| POLE |
| POLE |
| PREX2 |
| PRKAG2 |
| PTCH1 |
| PTEN-fluorescence_in_situ_hybridization_(fish) |
| PTEN-gene_mutation_analysis |
| PTEN |
| PTEN |
| PTPN13 |
| PTPRD |
| RAD51B |
| RAD51C |
| RAD51D |
| RAD52 |
| RAD54L |
| RANBP2 |
| RB1 |
| RB1 |
| RBM10 |
| RECQL4 |
| RET-fluorescence_in_situ_hybridization_(fish) |
| RET |
| RET |
| RICTOR |
| RNF43 |
| ROS1-fluorescence_in_situ_hybridization_(fish) |
| ROS1-md_dictated |
| ROS1 |
| RPTOR |
| RUNX1 |
| RUNX1T1 |
| RYR1 |
| RYR2 |
| SCN5A |
| SDHAF2 |
| SDHB |
| SDHC |
| SDHD |
| SETBP1 |
| SETD2 |
| SH2B3 |
| SLIT2 |
| SLX4 |
| SMAD3 |
| SMAD4 |
| SMAD4 |
| SMARCA4 |
| SOX9 |
| SPEN |
| STAG2 |
| STK11-gene_mutation_analysis |
| STK11 |
| STK11 |
| TAF1 |
| TBX3 |
| TCF7L2 |
| TERT |
| TET2 |

TABLE 1-continued

| |
|---|
| TGFBR1 |
| TGFBR2 |
| TGFBR2 |
| TMEM43 |
| TNNI3 |
| TNNT2 |
| TP53-gene_mutation_analysis |
| TP53-immunohistochemistry_(ihc) |
| TP53-md_dictated |
| TP53 |
| TP53 |
| TPM1 |
| TSC1 |
| TSC1 |
| TSC2 |
| TSC2 |
| VHL |
| WT1 |
| WT1 |
| XRCC3 |
| ZFHX |

A feature set for RNA related features may include features associated with raw read counts for every transcriptome of the human genome, features associated with normalized read counts for every transcriptome of the human genome, or features associated with normalized, encoded read counts, such as encoded via an autoencoder or a dimensionality reducer. Raw read counts may be accompanied by a normal value, identifying the expected number of read counts should the transcriptome be normally expressed. Raw read counts exceeding the normal value may be considered over expressed, and raw read counts falling below the normal value may be considered under expressed. Normalized read counts may be normalized to ensure that while every transcriptome has its own normal value, the resulting normalized value falls within a desired range that accounts for the differences between each unnormalized transcriptoms normal. For example, RPKM (Reads Per Kilobase Million), FPKM (Fragments Per Kilobase Million), or TPM (Transcripts Per Kilobase Million) may be used for normalization. RPKM may be calculated by scaling the total RNA reads of a specimen by 1,000,000 to create a scaling factor, scaling the total reads for any read counts for each read by the scaling factor to create an RPM, and dividing the RPM by the length of the gene to create an RPKM. FPKM may be generated by performing the same steps, but when performing pair-end sequencing, accounting for the fact that some reads may be counted twice. TPM may be calculated by performing the same steps but in a different order. First creating a reads per kilobase (RPK) by dividing read counts by the length of each gene, creating the scaling factor, and then dividing the RPK by the scaling factor to create the TPM.

Other normalization methods may be applied as well, such as one or more of the RNA normalization methods disclosed in U.S. Patent Publication 2020/0098448, titled "Methods of Normalizing and Correcting RNA Expression Data," filed Sep. 24, 2019, and published Mar. 26, 2020, the entire disclosure of which is hereby expressly incorporated by reference herein. Normalized, encoded read counts may be generated by first normalizing the RNA reads according to any of the above methods, and then passing the normalized read counts to an encoder or a dimensionality reducer, such as an autoencoder.

In one example, an autoencoder may reduce the dimensionality from 20,000+ transcriptomes to 100 encoded features, creatively named: rna_embedding-z_1 through rna_embedding-z_100. In one example, RNA related features for each transcriptome are generated from a sequencing of a patient's specimen. The number of encoded features may be any number where identifying the optimal number may include performing encoding for each of 2-9999 total number of encoded features, calculating a performance metric of each, and selecting the number of encoded features to be the number with the highest performance metric. A performance metric may include the accuracy of predictions made from the model using each total number of encoded features. Raw read counts may be between 0 reads and tens of thousands of reads. Normalization of the raw read counts from sequencing may convert the raw read scores to a value between from −0.5 to 0.5 where 0 represents the mean, or a normal expression value and −0.5 is lowest expression and 0.5 is highest expression. The normalized value may represent the number of standard deviations the raw read was from the normal reads expected in a patient such that −0.5 represents a high standard deviation below normal and 0.5 represents a high standard deviation above normal. In one example, RNA may be calculated on a gene or transcriptome basis where variants are not included. In another example, variants may be included, similar to DNA above.

Encoding normalized RNA reads may include generating a standard population finding or autoencoding. In one example, autoencoding may include utilizing a variational autoencoder, such as Beta-VAE or TC-VAE, or dimensionality reducers, such as SVD, PCA, or UMap. Outputs from an encoder, autoencoder, or dimensionality reducer may be presented as a matrix, where each row is for each patient, and each column is a normal distributed variable which may be interpreted as a ratio of patient's makeup in each population, such as values −0.25 to 0.25 or a standard deviation of 1, centered at 0. A patient's vector of deviations from normal may be interpreted to identify the makeup of the patient according to each population identified in the respective encoder. The matrix of normalized, encoded values may be supplied to a model for prediction of cardiac events without additional alterations.

Each of the models, raw RNA reads, normalized RNA reads, and normalized, encoded RNA reads may have differing operating characteristics, including speed and accuracy. For example, given the substantial reduced dimensionality from normalized, encoded RNA reads, one may expect the system to greatly improve processing speed at the cost of some degree of accuracy.

Combining all of the above input feature sets together from the ECG model, NGS model, and Observational models above results in an ROC AUC of approximately 0.70 which is greater than any of the models individually.

Figure 11:
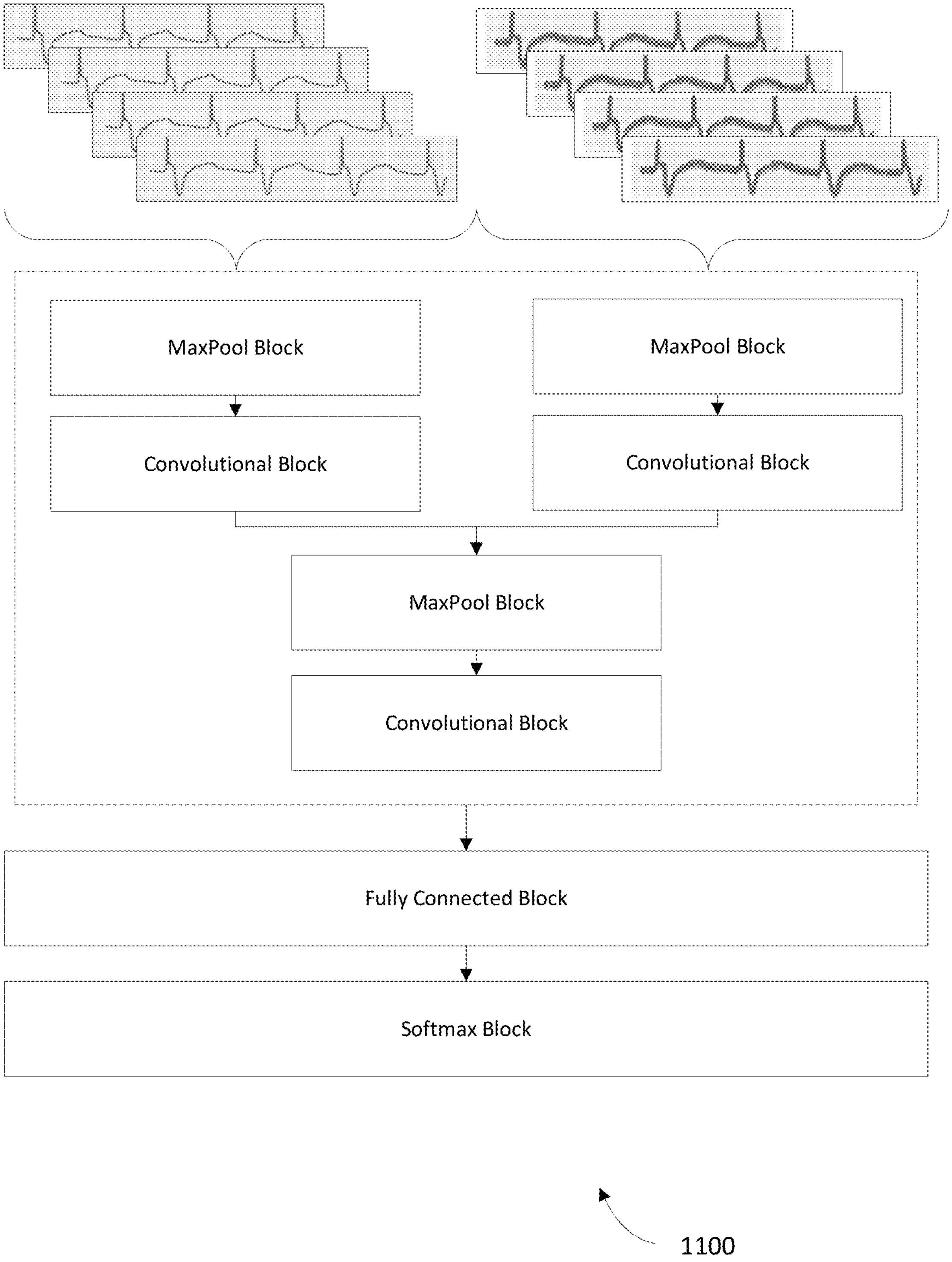
FIG. 11 illustrates an architecture of a convolutional neural network from which FFR Measurement predictions may be generated, in accordance with some embodiments of the present disclosure.

FIG. 11 illustrates an architecture of a convolutional neural network from which FFR Measurement predictions may be generated in accordance with some embodiments of the present disclosure. In one CNN architecture, the system 1100 may be utilize a plurality of 1D convolutional blocks, such as blocks receiving the ECG leads, with a batch normalization layer. Activation functions may be assigned as a restructure linear unit, and a batch size of 64 may be selected. Leads having 1250 signal values may be provided to a first branch and leads having 5000 signal values may be provided to a second branch. These two branches may then be provided to a fully connected convolutional layer which, in turn, may be connected to an output node with sigmoid function for prediction. A sigmoid function (not depicted, instead a softmax function is depicted) may receive additional information such as the age or sex of the patient, or a predicted FFR Measurement in order to improve the prediction reliability. In one example, an ADAM optimizer (not depicted) may be selected with a binary crossentropy loss function to train the model.

Figure 12:
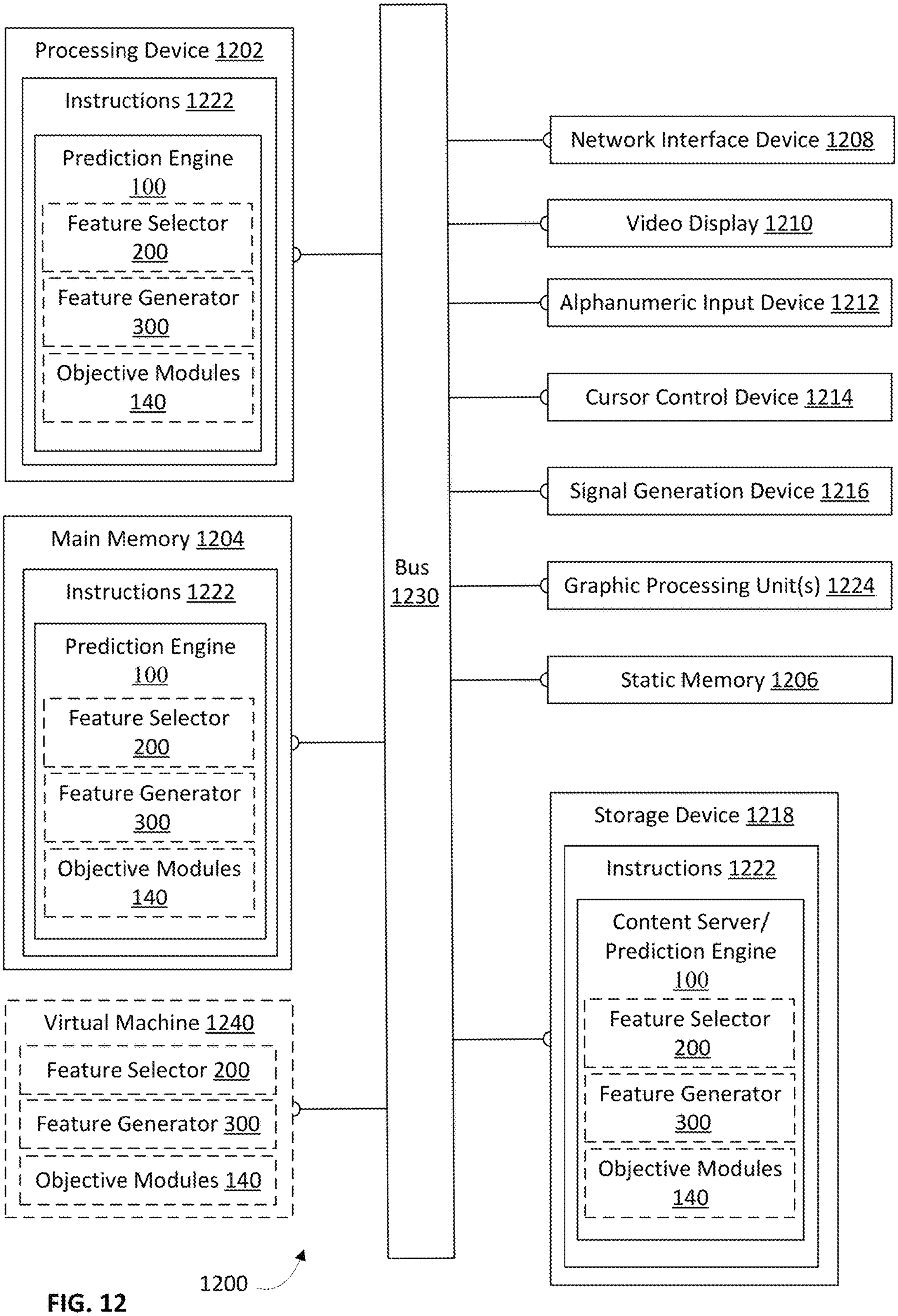
FIG. 12 is a block diagram of an example of a system in which some embodiments of the invention can be implemented.

FIG. 12 is an illustration of an example machine of a computer system 1200 within which a set of instructions, for causing the machine to perform any one or more of the methodologies discussed herein, may be executed. In some implementations, the machine may be connected (such as networked) to other machines in a LAN, an intranet, an extranet, and/or the Internet.

The machine may operate in the capacity of a server or a client machine in client-server network environment, as a peer machine in a peer-to-peer (or distributed) network environment, or as a server or a client machine in a cloud computing infrastructure or environment. The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 1200 includes a processing device 1202, a main memory 1204 (such as read-only memory (ROM), flash memory, dynamic random access memory (DRAM) such as synchronous DRAM (SDRAM) or DRAM, etc.), a static memory 1206 (such as flash memory, static random access memory (SRAM), etc.), and a data storage device 1218, which communicate with each other via a bus 1230.

Processing device 1202 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 1202 may also be one or more special-purpose processing devices such as an application specific integrated circuit (ASIC), a field programmable gate array (FPGA), a digital signal processor (DSP), network processor, or the like. The processing device 1202 is configured to execute instructions 1222 for performing the operations and steps discussed herein.

The computer system 1200 may further include a network interface device 1208 for connecting to the LAN, intranet, internee, and/or the extranet. The computer system 1200 also may include a video display unit 1210 (such as a liquid crystal display (LCD) or a cathode ray tube (CRT)), an alphanumeric input device 1212 (such as a keyboard), a cursor control device (such as, e.g., a mouse, joystick, or another control device, including a combination device), a signal generation device 1216 (such as, e.g., a speaker), and a graphic processing unit 1224 (such as, e.g., a graphics card).

The data storage device 1218 may be a machine-readable storage medium 1228 (also known as a computer-readable medium) on which is stored one or more sets of instructions or software 1222 embodying any one or more of the methodologies or functions described herein. The instructions 1222 may also reside, completely or at least partially, within the main memory 1204 and/or within the processing device 1202 during execution thereof by the computer system 1200, the main memory 1204 and the processing device 1202 also constituting machine-readable storage media.

In one implementation, the instructions 1222 include instructions for a prediction engine (such as the prediction engine 100, feature selector 200, feature generator 300, and objective modules 140 of FIG. 1) and/or a software library containing methods that function as a prediction engine. The instructions 1222 may further include instructions for a feature selector 200 and generator 300 and objective modules 140. While the machine-readable storage medium 1228 is shown in an example implementation to be a single medium, the term "machine-readable storage medium" should be taken to include a single medium or multiple media (such as a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media. The term "machine-readable storage medium" shall accordingly exclude transitory storage mediums such as signals unless otherwise specified by identifying the machine-readable storage medium as a transitory storage medium or transitory machine-readable storage medium.

In another implementation, a virtual machine 1240 may include a module for executing instructions for a feature selector 200 and generator 300 and objective modules 140. In computing, a virtual machine (VM) is an emulation of a computer system. Virtual machines are based on computer architectures and provide functionality of a physical computer. Their implementations may involve specialized hardware, software, or a combination of hardware and software.

Artificial Intelligence Engine Training Pipeline

An exemplary ME training pipeline may read in a configuration file (such as a JSON) with a number of operating parameters identified. Some parameters may be required while other parameters may be optional.

A pipeline may identify that one or more cohort files may be referenced for patient data such as a collection of cardiac event data, diagnosis and cardiac event data, or optional extra evaluation sets. The pipeline may also load one or more patient cohort files containing information about patient cardiac event details, including the date and occurrence of an event. The information may provide an indication, such as the date, or number of days since a patient last experienced an event. For a model of identifying FFR Measurement, the information may include an indication that a patient received an ECG.

The pipeline may identify which feature setts) are specified and queue up which feature set files for each patient may be loaded in order to access and use any relevant features. For example, if it specified that the pipeline is to train on a "staging" feature set, the pipeline may load a "Clinical" feature file, and subset all clinical data down to any staging features. If it is specified that the pipeline should use ECG features, the pipeline may load an imaging feature set and subset all imaging data down to any ECG features, such as voltages for each lead over time. The pipeline may select from any of the patient features disclosed herein and further may also join the feature sets from multiple relevant targets into a combined training feature set.

The pipeline may identify an upfront preprocessing function specified in the configuration file to preprocess the combined training feature set using the identified preprocessing. In one example, a preprocessing function may include one-hot-encoding of categorical features, normalizing features (e.g. condensing separate feature entries for related features, where condensing may include identifying the maximum of any two related columns as the normalized feature), removing uninformative features (e.g. features that just indicate if a field is missing, such as 'gender-missing', 'race-missing', or other status-unknown entries), removing features known to be misleading or problematic (e.g. sequencing normalization read-throughs), drop features with no variance, imputing missing values from other data (e.g. when the imputation is reliable), or other preprocessing methods.

The pipeline may identify a number of folds for training and subset which features will be used per collection of training set folds. In one example, the identification of the number of folds and subsetting, of features is based upon the combination of inline preprocessing method and feature selection method. In one example, a total of 5 folds may be selected, [0, 1, 2, 3, 4], one (e.g. fold 4) is kept as the hold out set, and the remaining 4 are used in training. Therefore, training sets may be identified for 5 total folds, including in one example:

- [0, 1, 2] which will be used to generate predictions for fold 3
- [0, 1, 3] which will be used to generate predictions for fold 2
- [0, 2, 3] which will be used to generate predictions for fold 1
- [1, 2, 3] which will be used to generate predictions for fold 0
- [0, 1, 2, 3] which will be used to generate predictions for the test set (fold 4)

Generating the combined feature sets for each fold, or the 5 different training sets defined above, may include, in one example, the following sequence of events:

1) Run the specified in-line preprocessing method using one or more of:
   a) Transformations to zero-center features (e.g. z-scoring)
   b) Transformations to scale features relative to the maximum observed value
   c) Dimensionality reduction (e.g. PCA)
   d) Subsetting to the top X correlated features to the target (where the target can be defined as the binary target, time until cardiac event for only patients who experience a cardiac event, the log of that duration, or another format).
2) Run the specified feature selection method on the in-line processed data using one or more of:
   a) A custom feature selection approach using Lasso modeling such as by re-sampling with replacement a number of times (e.g. 100 times) from each training subset (e.g. folds [0,1,2]), and fitting a lasso model on each bootstrap. For each lasso model, storing the features that were used in the model, and the associated regression coefficients. The features that are most important for any given training subset are the ones that appear in the most bootstrapped models, have high (in magnitude) coefficients, and have stable coefficients across models (in terms of the sign of the coefficient). In one example, identifying feature selection sets may include selecting the features that are occur in more than a minimum percentage (e.g. 50%) of bootstraps, have the same sign of their coefficient at least some minimum percent (e.g. 90%) of the time that they are used.
   b) A custom recursive feature elimination framework, such as by running a model on all features (or subset of features if defined in the inline preprocessing method), dropping the bottom (e.g. 10%) of features as ranked by their model coefficients, and repeating the feature elimination until a threshold number of features is met (e.g. 10, 50, 200, 5000). At each step of the process, each feature's rank is stored. At the end (once only Y features remain), the original combined feature set may be ranked, each by their average rank from this process, and only the top Z (e.g. 40) features may be selected as features for that training subset. Recursive feature elimination may include logistic regression, cox proportional hazards, early stopping, ranking/selection methods, and others.
3) Storing the selected features for use in each fold.
4) Optimizing hyperparameters, such as a gridsearch for the set of hyperparameters using one or more of:
   a) logistic regression
      i) identifying regularization strength in the range 100, 10, 1, 0.1, 0.01, and 0.001.
   b) cox proportional hazards
   c) random forest
      i) number of trees, such as 20, 40, 60, or 80.
      ii) maximum depth of each tree, such as 2, 3, 4, 10, 20, 100, branches.
      iii) minimum samples per leaf, such as 5, 6, 7, 10, 100
      iv) The metric to optimize for. For example, ROC AUC or concordance index.
5) The pipeline may cycle through all the training subsets, for example, the four training subsets [0, 1, 2], [0, 1, 3], [0, 2, 3], and [1,2,3]), using the normalized and selected feature sets. Then, for each possible hyperparameter space, fitting the identified model on the training subset, predict on the remaining training fold, and storing the resulting the metric which is being optimized for (e.g. ROC AIX, concordance index) on the held out fold. Each search space (e.g. the combined training subset metric results) may then be associated with 4 out of fold metrics. The hyperparameter set that leads to the best average metric (averaged across those 4 out of fold estimates) is stored as the optimal hyperparameters of the model.
6) The pipeline may generate the final prediction on the test fold using the combined feature selected subset from each fold and the model identified with the optimal hyperparameters for the model to predict the output on the test fold and store the predictions.
7) Identify and store features which were most important in driving the predictions, based on the feature selection method(s) selected using one or more of:
   a) Spearman correlation between the feature and predictions,
   b) Pearson correlation between the feature and predictions,
   c) Kendall correlation between the feature and predictions,
   d) Custom subset aware feature effect correlation identification,
   e) Nulling-out method where all values of a feature may be set to 0, and compute the mean absolute deviation in resulting probabilities based on the rest of the features.

8) The prediction results may be stored in one or more patient information databases and all stored metrics may be saved to the pipeline as a model for predicting future cardiac event site occurrence in a new patient.

Models may be generated for any combination of features based upon the best performance to patients having a representative selection of features a model has been trained on. Each patient has a unique feature set based upon their interactions with the medical system and length of time in the medical system. While it is impossible to exhaustively list every combination of features, patients tend to bin into a set of feature sets. As the medical industry advances and more feature sets are curated for more patients, the models listed here may be increased. Accordingly, a patient may be selected for a model comprising features wherein the patient features include: raw RNA reads, normalized RNA reads, autoencoded RNA reads, RNA related features, any RNA related features with any other RNA related features, DNA reads, normalized DNA reads, autoencoded DNA reads, DNA related features, any DNA related features with any other DNA related features, any RNA related features with any DNA related features, RNA and DNA reads, RNA and DNA related features, RNA reads and imaging features, RNA related features and imaging features, DNA reads and imaging features, DNA related features and imaging features, cfDNA reads, cfDNA related features, cfDNA reads and imaging features, cfDNA related features and imaging features, cfDNA reads and clinical features, cfDNA related features and clinical features, cfDNA reads and combined clinical and imaging features, cfDNA related features and combined clinical and imaging features, cfDNA related features and RNA related features, cfDNA related features and DNA related features, combined RNA and DNA reads and imaging features, combined RNA and DNA related features and imaging features, RNA reads and clinical features, RNA related features and clinical features, DNA reads and clinical features, DNA related features and clinical features, imaging features and clinical features, RNA reads and combined imaging and clinical features, RNA related features and combined imaging and clinical features, DNA reads and combined imaging and clinical features, DNA related features and combined imaging and clinical features, combined RNA and DNA reads and combined imaging and clinical features, any combined RNA and DNA related features and combined imaging and clinical features, any RNA related features with any proteomic features, and DNA related features with any proteomic features, combined RNA and DNA related features with any proteomic features, any DNA related features combined with imaging features and proteomic features, any DNA related features combined with clinical features and proteomic features, any RNA related features combined with imaging features and proteomic features, any RNA related features combined with clinical features and proteomic features, and any combined RNA and DNA related features combined with combined clinical and imaging features and proteomic features, and any of the foregoing feature combinations with ECG features. While some combinations have been inadvertently left out of the above listing of combinations of features, it should be appreciated that a full combinatorial listing of features from each of the above features to each other of the above features is attempted and desired. It should also be appreciated that a full combinatorial listing of the features from feature store 120 is similarly disclosed as applicable models to the artificial intelligence engine as disclosed herein.

It should be understood that RNA related features may include raw RNA reads, normalized RNA reads, and autoencoded RNA reads and that DNA related features may include raw DNA reads, normalized DNA reads, and autoencoded DNA reads. Therefore combined RNA and DNA related features may include any combination raw RNA reads to raw DNA reads, normalized DNA reads, and autoencoded DNA reads, normalized RNA reads to raw DNA reads, normalized DNA reads, and autoencoded DNA reads, autoencoded RNA reads to raw DNA reads, normalized DNA reads, and autoencoded DNA reads and vice versa.

The methods and systems described above may be utilized in combination with or as part of a digital and laboratory health care platform that is generally targeted to medical care and research, and in particular, generating a molecular report as part of a targeted medical care precision medicine treatment or research. It should be understood that many uses of the methods and systems described above, in combination with such a platform, are possible. An example of such a platform is described in U.S. Patent Publication No, 2021/0090694, titled "Data Based Cancer Research and Treatment Systems and Methods" (hereinafter "the '694 publication"), which is incorporated herein by reference in its entirety for all purposes. In some aspects, a physician or other individual may utilize an artificial intelligence engine, such as the system 100 for generating and modeling predictions of patient objectives, in connection with one or more expert treatment system databases shown in FIG. 1 of the '694 publication. The artificial intelligence engine of system 100 may operate on one or more microservices operating as part of systems, services, applications, and integration resources database, and the methods described herein may be executed as one or more system orchestration modules/resources, operational applications, or analytical applications. At least some of the methods (e.g., microservices) can be implemented as computer readable instructions that can be executed by one or more computational devices, such as the artificial intelligence engine of system 100. For example, an implementation of one or more embodiments of the methods and systems as described above may include microservices included in a digital and laboratory health care platform that can generate predictions of a patient's likelihood to cardiac event within a time period based upon the patient's available features and sequencing results.

In some embodiments, a system may include a single microservice for executing and delivering the predictions or may include a plurality of microservices, each microservice having a particular role which together implement one or more of the embodiments above. In an example, a first microservice may include extracting patient information from one or more patients, identifying one or more interactions for each of the one or more patients based at least in part on the received patient information; generating, for one or more targets at each one or more interactions, one or more timeline metrics identifying whether each of the one or more targets occurs within a time period of an occurrence of the interaction; identifying, for each timeline metric of the one or more timeline metrics, whether a patient will be associated with one or more status characteristics within the time period; training a target prediction model for each of the one or more targets based at least in part on the one or more status characteristics; and associating predictions for each patient from the target prediction model for each of the one or more targets with a respective one or more timeline metrics of the one or more timeline metrics. A second microservice may include listening for an order to generate a prediction using the artificial intelligence engine of system 100 for a new patient using the trained model. Similarly, the second microservice may include providing the received information to the trained prediction model for the identified target/objective and generating a prediction so that the artificial intelligence engine of system 100 may provide the prediction in response to the order according to an embodiment, above.

The artificial intelligence engine of system 100 may be utilized as a source for automated data generation of the kind identified in FIG. 59 of the '694 publication. For example, the artificial intelligence engine of system 100 may interact with an order intake server to receive an order for a test, such as a test that provides predictions with respect to a patient. Where embodiments above are executed in one or more microservices with or as part of a digital and laboratory health care platform, one or more of such microservices may be part of an order management system that orchestrates the sequence of events as needed at the appropriate time and in the appropriate order necessary to instantiate embodiments above.

For example, continuing with the above first and second microservices, an order management system may notify the first microservice that an order for a test has been received and is ready for processing. The first microservice may include executing and notifying the order management system once the delivery of any patient information for the second microservice is ready, including one or more interactions, one or more timeline metrics, and a target/objective pair. Furthermore, the order management system may identify that execution parameters (prerequisites) for the second microservice are satisfied, including that the first microservice has completed, and notify the second microservice that it may continue processing the order to provide the prediction from the artificial intelligence engine of system 100 according to an embodiment, above. While two microservices are utilized for illustrative purposes, patient information extraction, interaction identification, status characteristic identification, model training, and patient predictions may be split up between any number of microservices in accordance with performing embodiments herein, The digital and laboratory health care platform further includes one or more insight engines shown in FIG. 272 of the '694 publication. Exemplary insight engines may include a human leukocyte antigen (HLA) loss of homozygosity (LOH) engine, a PD-L1 status engine, a homologous recombination deficiency (HRD) engine, a cellular pathway activation report engine, an immune infiltration engine, a microsatellite instability engine, a pathogen infection status engine, and so forth as described with respect to FIGS. 189, 199-200, and 266-270 of the '694 publication. In an aspect, a model may be trained on and subsequently receive as an input for predictions, features including diagnosis of the patient as to an insight engine such as HLA LOH, PD-L1, HRD, active pathway, or other insight status. The artificial intelligence engine of system 100 may identify a patient having features from an insight engine and select an appropriate model and feature set to utilize the features in a prediction.

When the digital and laboratory health care platform further includes a molecular report generation engine, the methods and systems described above may be utilized to create a summary report of a patient's genetic profile and the results of one or more insight engines for presentation to a physician. For instance, the report may provide to the physician information about the extent to which the specimen that was sequenced contained tumor or normal tissue from a first organ, a second organ, a third organ, and so forth. For example, the report may provide a genetic profile for each of the tissue types, tumors, or organs in the specimen. The genetic profile may represent genetic sequences present in the tissue type, tumor, or organ and may include variants, expression levels, information about gene products, or other information that could be derived from genetic analysis of a tissue, tumor, or organ via a genetic analyzer. The report may further include therapies and/or clinical trials matched based on a portion or all of the genetic profile or insight engine findings and summaries shown in FIGS. 271 and 302 of the '694 publication.

It should be understood that the examples given above are illustrative and do not limit the uses of the systems and methods described herein in combination with a digital and laboratory health care platform.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "providing" or "calculating" or "determining" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMS), EPROMs, EEPROMs, magnetic or optical cards, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct a more specialized apparatus to perform the method. The structure for a variety of these systems will appear as set forth in the description below. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (such as a computer). For example, a machine-readable (such as computer-readable) medium includes a machine (such as a computer) readable storage medium such as a read only memory ("ROM"), random access memory ("RAM"), magnetic disk storage media, optical storage media, flash memory devices, etc.

In the foregoing specification, implementations of the disclosure have been described with reference to specific example implementations thereof. It will be evident that various modifications may be made thereto without departing from the broader spirit and scope of implementations of the disclosure as set forth in the following claims. The specification and drawings are, accordingly, to be regarded in an illustrative sense rather than a restrictive sense.

What is claimed is:

1. A method comprising:

receiving, to one or more processors, electrocardiogram signal data for a subject;

receiving, to the one or more processors, observational subject feature data for the subject;

training a machine learning engine comprising a fractional flow reserve (FFR) model on a training electrocardiogram signal data set and a training observational subject feature data set to predict fractional flow reserve measurements at a plurality of different cardiac locations;

applying, in the one or more processors, the electrocardiogram signal data for the subject and the observational subject feature data for the subject to the trained machine learning engine comprising the FFR model to predict probabilities of stenosis at a plurality of different cardiac locations for the subject within a time period;

evaluating each probability relative to one or more threshold probabilities in order to classify each probability; and generating an electronic report to relay predicted probabilities.

2. The method of claim 1, wherein the stenosis comprises lesions.

3. The method of claim 1, wherein the received electrocardiogram signal data is a subset of a larger set of electrocardiogram signal data received to the one or more processors, and wherein the received electrocardiogram signal data is selected for use with the FFR model as a result of the training of the FFR model.

4. The method of claim 1, wherein the received observational subject feature data is a subset of a larger set of observational subject feature data received to the one or more processors, and wherein the received observational subject feature data is selected for use with the FFR model as a result of the training of the FFR model.

5. The method of claim 1, wherein the electrocardiogram signal data comprises short lead electrocardiogram signal data and/or long lead electrocardiogram signal data.

6. The method of claim 1, wherein the short lead electrocardiogram signal data comprises 1250 signal values per short lead and the long lead electrocardiogram signal data comprises 5000 signal values per long lead.

7. The method of claim 1, wherein the observational subject feature data comprises image feature data comprising IHC slide image data or H&E slide image data.

8. The method of claim 1, wherein the observational subject feature data comprises RNA transcriptome data including one or more of raw sequencing results, transcriptome expressions, genes, mutations, variant calls, or variant characterizations, or DNA-derived data including one or more of raw sequencing results, genes, mutations, variant calls, or variant characteristics.

9. The method of claim 1, wherein the observational subject feature data comprises genetic variants data determined for gene sequencing data of a sample.

10. The method of claim 1, wherein the observational subject feature data comprises genetic variants data that identifies single or multiple nucleotide polymorphisms, identifies whether a variation is an insertion or deletion event, identifies loss or gain of function, identifies fusions, is copy number variation data, is microsatellite instability data, or is structural variations within DNA or RNA data.

11. The method of claim 1, wherein the observational subject feature data comprises data indicating one or more of diagnosis, symptoms, therapies, outcomes, subject demographics such as subject name, date of birth, gender, ethnicity, date of death, address, smoking status, diagnosis dates for heart disease, stenosis, atrial fibrillation, hemodynamic alteration, coronary artery disease, cancer, illness, disease, diabetes, depression, other physical or mental maladies, personal medical history, family medical history, clinical diagnoses such as date of initial diagnosis, treatments and outcomes such as line of therapy, therapy groups, clinical trials, medications prescribed or taken, surgeries, radiotherapy, imaging, adverse effects, associated outcomes, genetic testing and laboratory information such as performance scores, lab tests, pathology results, prognostic indicators, date of genetic testing, testing provider used, testing method used, such as genetic sequencing method or gene panel, gene results, such as included genes, variants, expression levels/statuses, or corresponding dates associated thereof.

12. The method of claim 1, wherein the observational subject feature data comprises proteomic data, transcriptome data, epigenomic data, metabolomics data, or microbiome data.

13. The method of claim 1, wherein the observational subject feature data comprises organoid derived data.

14. The method of claim 1, wherein the observational subject feature data comprises data indicating subject symptoms, diagnosis, treatments, medications, therapies, hospice, responses to treatments, laboratory testing results, medical history, geographic locations of each, demographics, or other features of the subject which may be found in the subject's medical record.

15. The method of claim 1, wherein the trained machine learning engine comprising an FFR model comprises one or more gradient boosting models, one or more random forest models, one or more convolution neural networks (CNNs), one or more neural networks (NN), one or more regression models, one or more Naive Bayes models, or one or more machine learning algorithms (MLA).

16. The method of claim 1, wherein the trained machine learning engine is a CNN comprising a plurality of 1D convolutional blocks receiving the electrocardiogram signal data.

17. The method of claim 16, wherein the trained machine learning engine is a CNN comprising a first branch of 1D convolutional blocks for receiving short lead electrocardiogram signal data and a second branch of 1D convolutional blocks for receiving long lead electrocardiogram signal data.

18. The method of claim 17, wherein the CNN comprises a fully connected convolutional layer connected to an output of the first branch and an output of the second branch and connected to an output node with a softmax function layer for generating the probabilities of the target cardiac outcome.

19. The method of claim 18, wherein applying the electrocardiogram signal data and the observational subject feature data to the trained machine learning engine comprises: applying the electrocardiogram signal data to the plurality of 1D convolutional blocks and applying the observational subject feature data to the softmax function layer.

20. The method of claim 1, wherein the trained machine learning engine is a CNN comprising a first branch of 1D convolutional blocks for receiving short lead electrocardiogram signal data, a second branch of 1D convolutional blocks for receiving long lead electrocardiogram signal data, a third branch of 1D convolutional blocks for receiving the observational subject feature data, and a fully connected convolutional layer connected to each branch connected to an output node with a softmax function layer for generating the probabilities of the target cardiac outcome.

21. The method of claim 1, wherein receiving the electrocardiogram signal data comprises receiving the electrocardiogram signal data from an electrocardiogram apparatus over a communication network.

22. The method of claim 1, wherein the one or more processors are located in a cloud-based server, and wherein receiving the electrocardiogram signal data comprises receiving the electrocardiogram signal data from an electrocardiogram apparatus communicatively coupled to the cloud-based server via a cloud network.

23. A cloud-based server configured to perform the method of claim 1.

24. A microservice stored on a computer readable medium of a computing device having the one or more processors, the microservice being executable on the computing device to perform the method of claim 1.

25. The method of claim 1, wherein receiving the observational patient feature data comprises receiving the observational subject feature data from an electronic medical record (EMR), a pathology report, radiology report, and/or molecular data report.

26. The method of claim 1, comprising:

transmitting the electronic report to a user over a computer network in real time, so that the user has immediate access to the electronic report; and displaying the information contained in the electronic reporting in a user interface displayed on the user's display.

27. The method of claim 1, wherein the electronic report is generated as part of a precision medicine result delivery for the subject.

28. The method of claim 1, wherein the electronic report comprises a recommendation to a physician to treat the subject using a treatment that correlates with the target cardiac outcome.

29. The method of claim 1, wherein the electronic report comprises a recommendation to a physician to select a treatment which provides adjustments to a typical monitoring including one or more of scanning, imaging, and blood testing.

30. The method of claim 1, wherein the electronic report includes a cardiac model, indicators on the cardiac model at one or more of the plurality of different cardiac locations reflecting the classification of the probability of stenosis at that location, and visual representations of the predicted probabilities.

* * * * *